United States Patent
Lim et al.

(10) Patent No.: US 10,355,221 B2
(45) Date of Patent: Jul. 16, 2019

(54) HETEROCYCLIC COMPOUND AND ORGANIC SOLAR CELL COMPRISING THE SAME

(71) Applicant: LG CHEM, LTD., Seoul (KR)

(72) Inventors: Bogyu Lim, Daejeon (KR); Doowhan Choi, Daejeon (KR); Jaechol Lee, Daejeon (KR); Keun Cho, Daejeon (KR)

(73) Assignee: LG Chem, Ltd. (KR)

( * ) Notice: Subject to any disclaimer, the term of this patent is extended or adjusted under 35 U.S.C. 154(b) by 30 days.

(21) Appl. No.: 14/771,056

(22) PCT Filed: Apr. 10, 2015

(86) PCT No.: PCT/KR2015/003608
§ 371 (c)(1),
(2) Date: Aug. 27, 2015

(87) PCT Pub. No.: WO2015/163614
PCT Pub. Date: Oct. 29, 2015

(65) Prior Publication Data
US 2016/0372680 A1 Dec. 22, 2016

(30) Foreign Application Priority Data
Apr. 21, 2014 (KR) .......... 10-2014-0047209

(51) Int. Cl.
*C07D 519/00* (2006.01)
*H01L 51/00* (2006.01)
(Continued)

(52) U.S. Cl.
CPC ........ *H01L 51/0072* (2013.01); *C07D 417/14* (2013.01); *C07D 487/04* (2013.01); *C07D 495/04* (2013.01); *C07D 519/00* (2013.01); *C07F 7/0812* (2013.01); *C07F 7/0816* (2013.01); *H01L 51/0053* (2013.01); *H01L 51/0068* (2013.01); *H01L 51/0071* (2013.01);
(Continued)

(58) Field of Classification Search
USPC .................................. 136/243–265
See application file for complete search history.

(56) References Cited

U.S. PATENT DOCUMENTS

| 5,331,183 A | 7/1994 | Sariciftci et al. |
| 5,454,880 A | 10/1995 | Sariciftci et al. |
| 2012/0024382 A1* | 2/2012 | Holmes ............... C07C 13/567 136/263 |

FOREIGN PATENT DOCUMENTS

| CN | 103087056 | 5/2013 |
| CN | 103087056 A1 * | 5/2013 |

(Continued)

OTHER PUBLICATIONS

Love et al. "Silaindacenodithiophene-Based Molecular Donor: Morphpological Features and Use in the Fabrication of Compositionally Tolerant, High-Efficiency Bulk Heterojunction Solar Cells" J. Am. Chem. Soc. 136, pp. 3597-3606 (Feb. 13, 2014).*

(Continued)

*Primary Examiner* — Dustin Q Dam
(74) *Attorney, Agent, or Firm* — Myers Bigel, P.A.

(57) ABSTRACT

The present specification relates to a heterocyclic compound and an organic solar cell including the same.

13 Claims, 9 Drawing Sheets

(51) Int. Cl.
C07D 417/14 (2006.01)
C07D 487/04 (2006.01)
C07D 495/04 (2006.01)
C07F 7/08 (2006.01)
H01L 51/42 (2006.01)

(52) U.S. Cl.
CPC ...... *H01L 51/0074* (2013.01); *H01L 51/0094* (2013.01); *H01L 51/0037* (2013.01); *H01L 51/4253* (2013.01); *H01L 2251/308* (2013.01); *Y02E 10/549* (2013.01)

(56) References Cited

FOREIGN PATENT DOCUMENTS

CN 103087083 A 5/2013
CN 183087083 5/2013

OTHER PUBLICATIONS

Gadisa et al. ("Effect of Alkyl Side-Chain Length of Photovoltaic Properties of Poly(3-alkylthiophene)/PCBM Bulk Heterojunctions" Adv. Funct. Mater. 19 (Year: 2009).*
"Optimization of energy levels by molecular design:evaluation of bis-diketopyrrolopyrrole molecular donor materialsfor bulk heterojunction solar cells†‡" ; Walker, et al.; Energy Environ. Sci., 2013, 6, 952.
"Synthesis of low bandgap polymers based on thienoquinodimethane units and their applications in bulk heterojunction cells†"; Umeyama, et al.; J. Mater. Chem., 2012, 22, 24394.
"Solar Cell Efficiency, Self-Assembly, and Dipole-Dipole Interactions of Isomorphic Narrow-Band-Gap Molecules"; Takacs, et al; J. Am. Chem. Soc. 2012, 134, 16597-16606.
Kang, et al.: "High Crystalline Dithienosilole-Cored Small Molecule Semiconductor for Ambipolar Transistor and Nonvolatile Memory", XP-055393289, ACS Applied Materials & Interfaces, vol. 6, No. 9, Apr. 7, 2014, pp. 6589-6597.
Bai, et al.: "A bipolar small molecule based on indacenodithiophene and diketopyrrolopyrrole for solution processed organic solar cells", XP-055393547, Journal of Materials Chemistry A: Materials for energy and sustainability, vol. 2, No. 3, Jan. 1, 2014, pp. 778-784.
Shi-Yong Liu et al., "C—H Activation: making diketopyrrolopyrrole derivatives easily accessible", J. Mater. Chem. A 1: 2795-2805 (2013).
Zhi Li et al., "Solution Processable Rhodanine-Based Small Molecule Organic Photovoltaic Cells with a Power Conversion Efficiency of 6.1%", Adv. Energy Mater. 2: 74-77 (2012).
Kerstin Schulze et al., "Efficient Vacuum-Deposited Organic Solar Cells Based on a New Low-Bandgap Oligothiophene and Fullerene C60", Adv. Mater. 18: 2872-2875 (2006).
Zheng et al. "Impact of Alkyl Chain Length on Small Molecule Crystallization and Nanomorphology in Squaraine-Based Solution Processed Solar Cells" The Journal of Physical Chemistry 121:7750-7760 (2017).
Walker et al. "Effect of Heterocyclic Anchoring Sequence of the Properties of Dithienogermole-Based Solar Cells" Applied Materials & Interfaces 9:7091-7099 (2017).
Ha et al. "Synthesis and Characterization of Naphthalene End-capped Triethylsilylethynyl Anthradithiopene for Organic Thing-Film Transistors" Bulletin of the Korean Chemical Society 36:2051-2054 (2015).
Bin et al. "9.73% Efficiency Nonfullerene All Organic Small Molecule Solar Cells with Absorption-Complementary Donor and Acceptor" Journal of the American Chemical Society 139:5085-5094 (2017).
Deng et al. "Fluorination-enabled optimal morphology leads to over 11% efficiency for inverted small-molecule organic solar cells" Nature Communications 7(13740):1-9 (2016).
Locklin et al. "Organic Thin Film Transistors Based on Cyclohexyl-Substituted Organic Semiconductors" Chemistry of Materials 17:3366-3374 (2005).
Usta et al. "Polymeric and Small-Molecule Semiconductors for Organic Field-Effect Transistors" Large Area and Flexible Electronics, First Edition :3-99 (2015).
Gadisa et al. "Effect of Alkyl Side-Chain Length on Photovoltaic Properties of Poly(3-alkylthiophene)/PCBM Bulk Heterojunctions " Advanced Functional Materials 19:3300-3306 (2009).
Friedel et al. "Influence of Alkyl Side-Chain Length on the Performance of Poly(3-alkylthiophene)/Polyfluorene All-Polymer Solar Cells" Chemistry of Materials 22:3389-3398 (2010).
Kaneto et al. "Alkyl Chain Length Dependence of Filed-Effect Mobilities in Regioregular Poly(3-Alkylthiophene) Films" Japanese Journal of Applied Physics 39:L 872-L874 (2000).
Urien et al. "Effect of the regioregularity of poly(3-hexylthiophene) on the performances of organic photovoltaic devices" polymer international 57:764-769 (2008).
Kline et al. "Dependence of Regioregular Poly(3-hexylthipene Film Morphology and Filed-Effect Mobility on Molecular Weight" Macromolecules 38:3312-3319 (2005).
Zou et al. "Synthesis and Characterization of New Low-Bandgap Diketopyrrolopyrrole-Based Copolymers" Macromolecules 42:6361-6365 (Jul. 14, 2009).

* cited by examiner

[Figure 1]
[Figure 2]
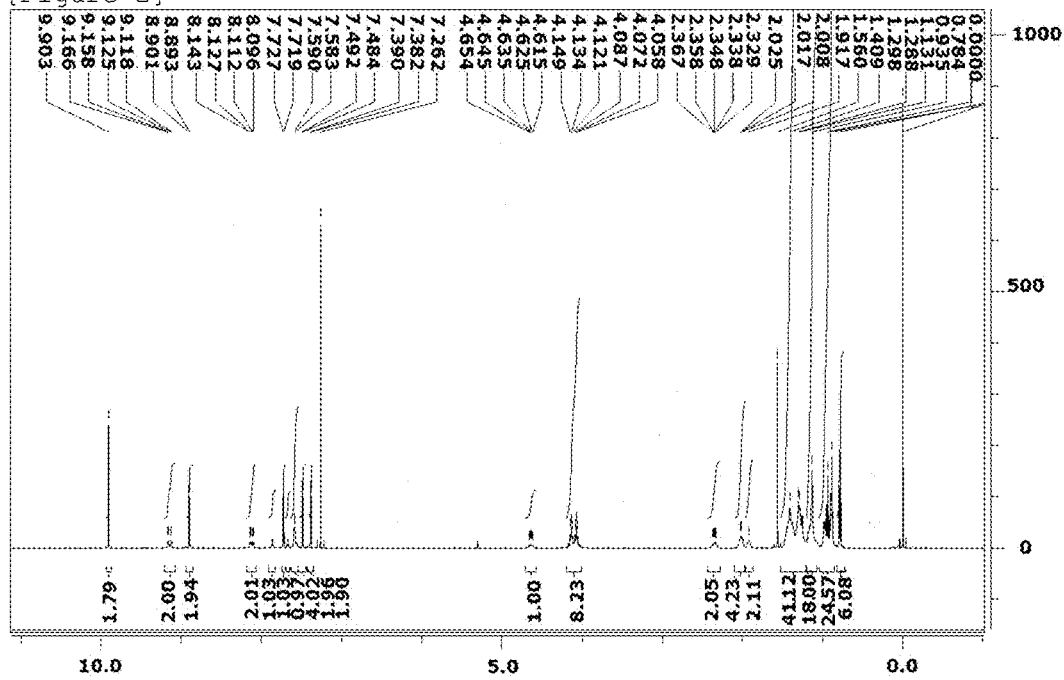

[Figure 3]
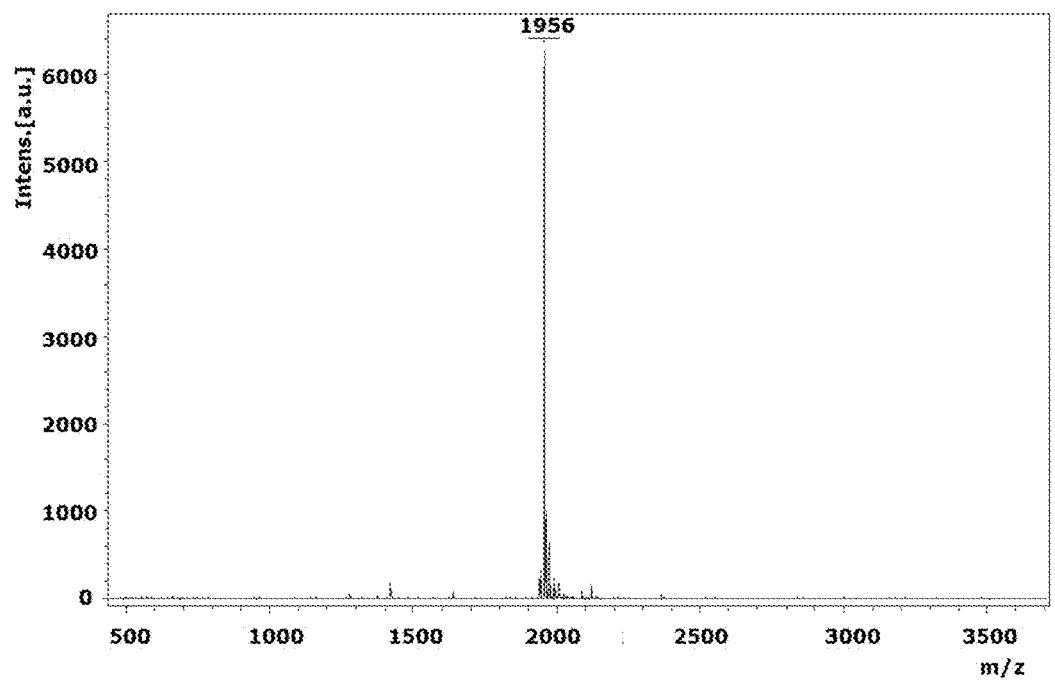
[Figure 4]
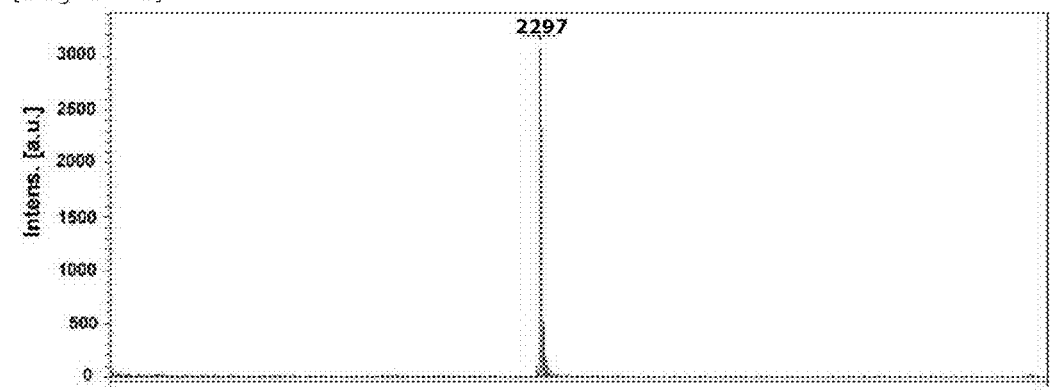

[Figure 5]
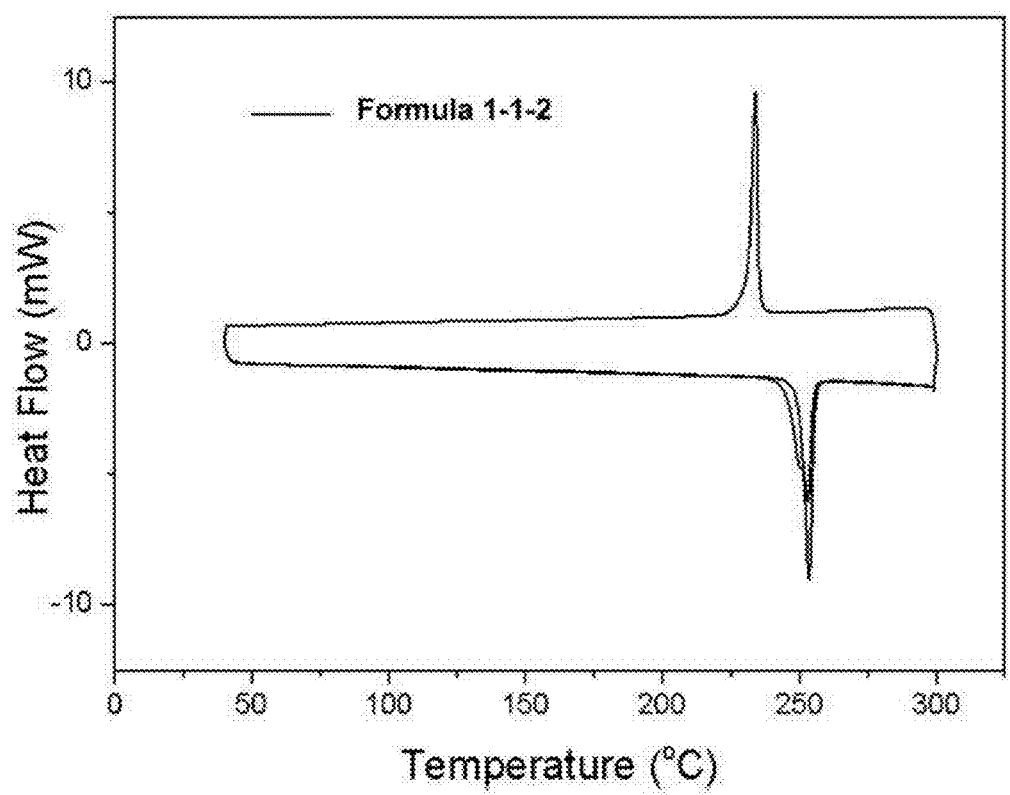

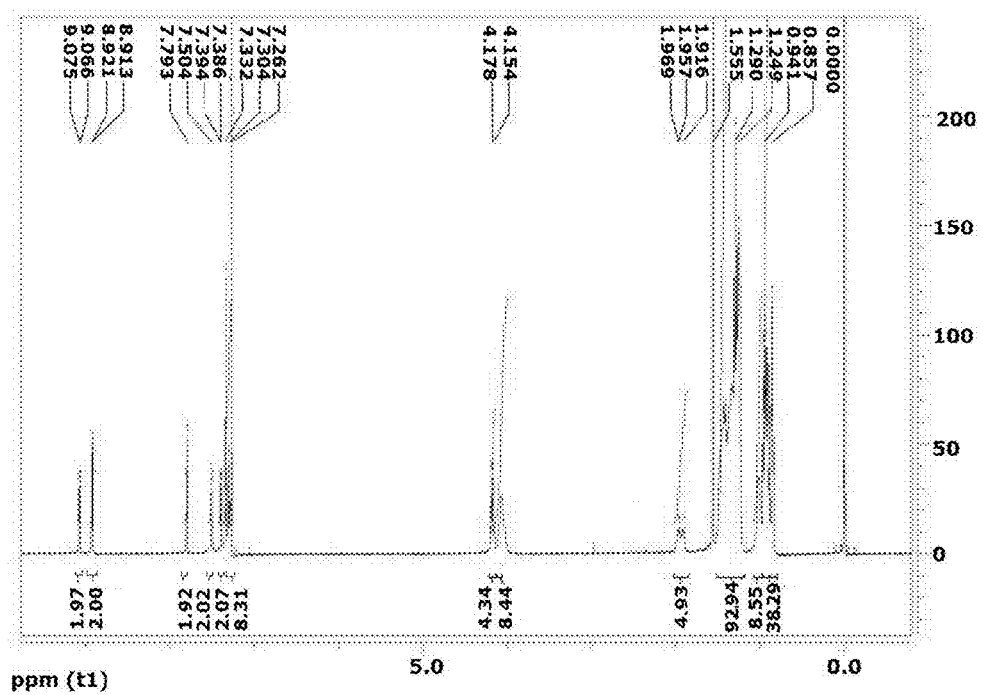
[Figure 6]

[Figure 7]
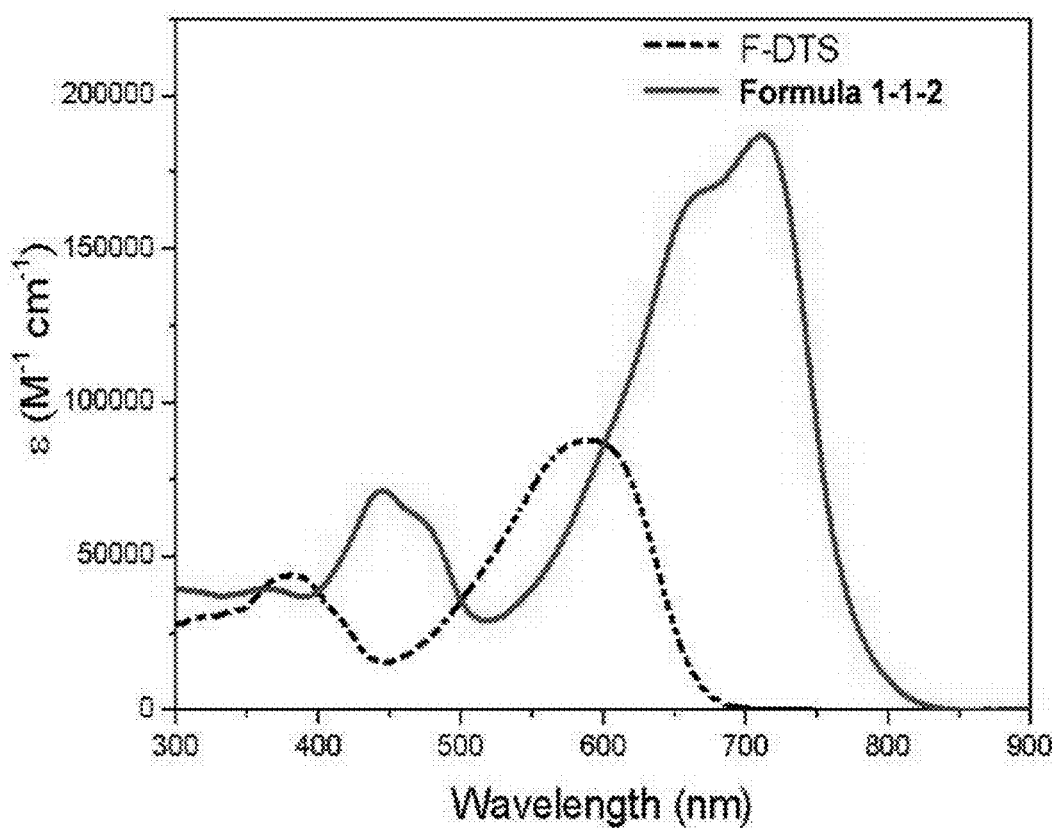

[Figure 8]
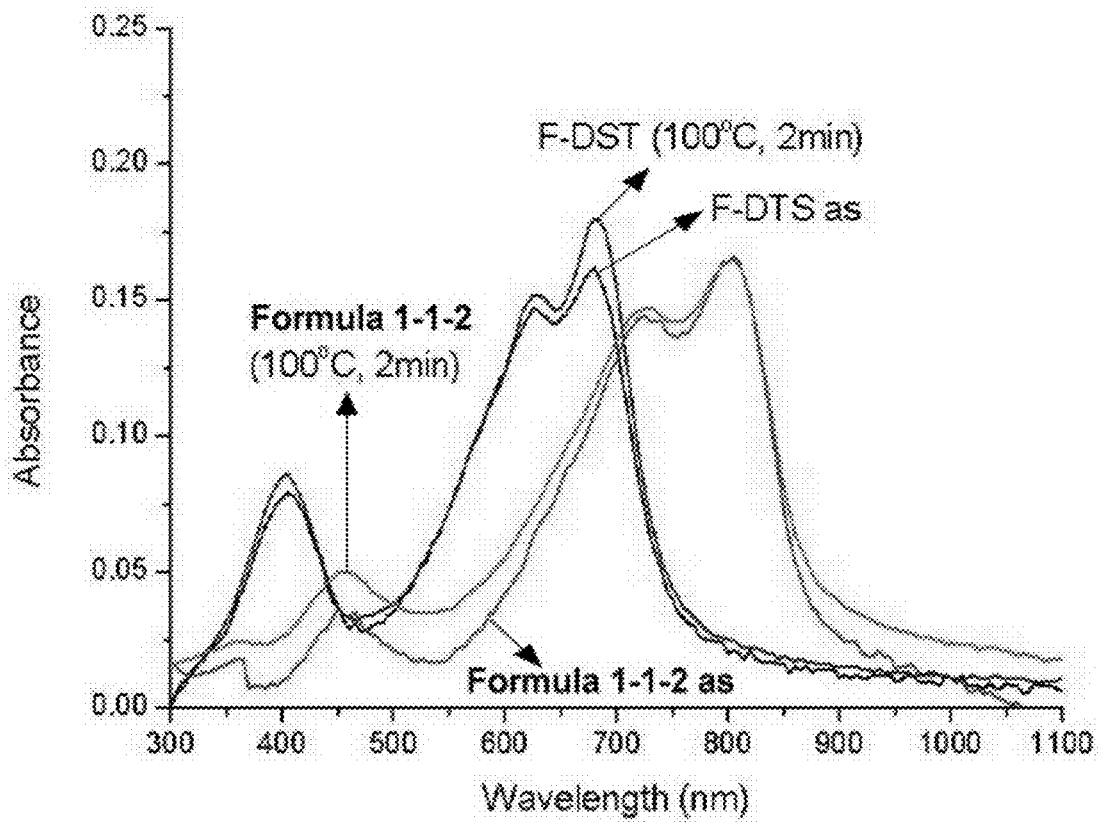
[Figure 9]
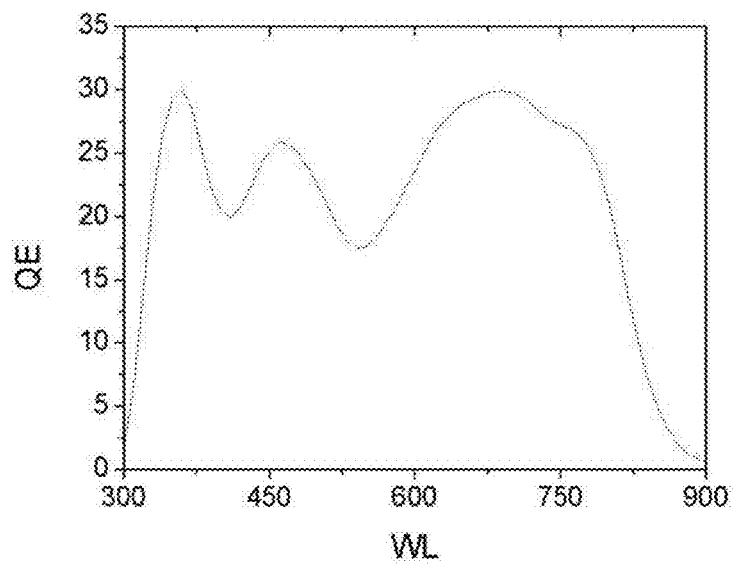

[Figure 10]
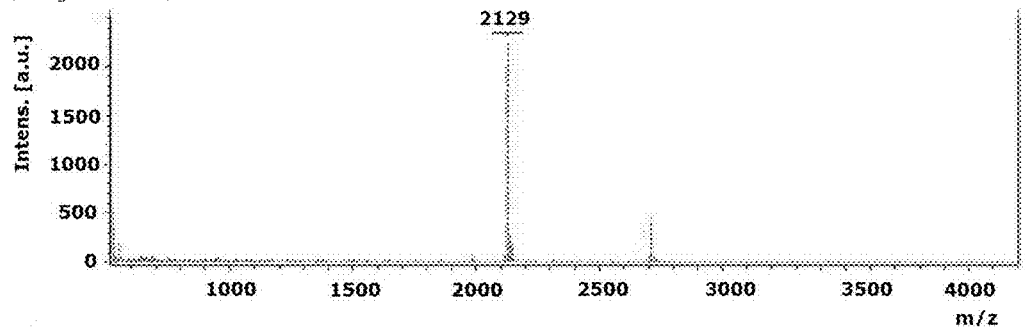
[Figure 11]
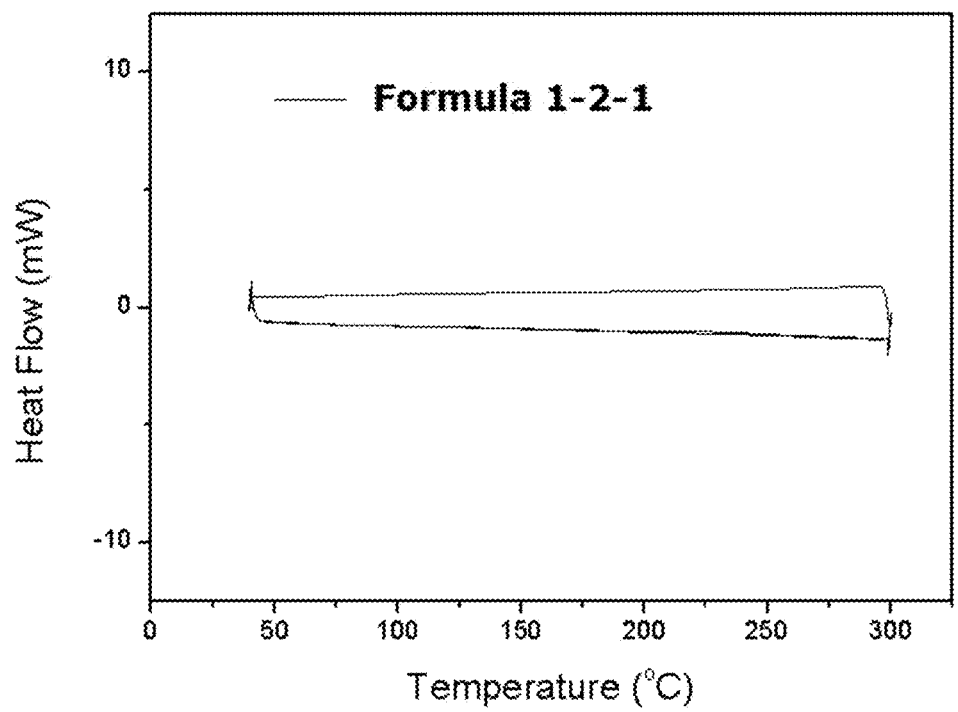

[Figure 12]
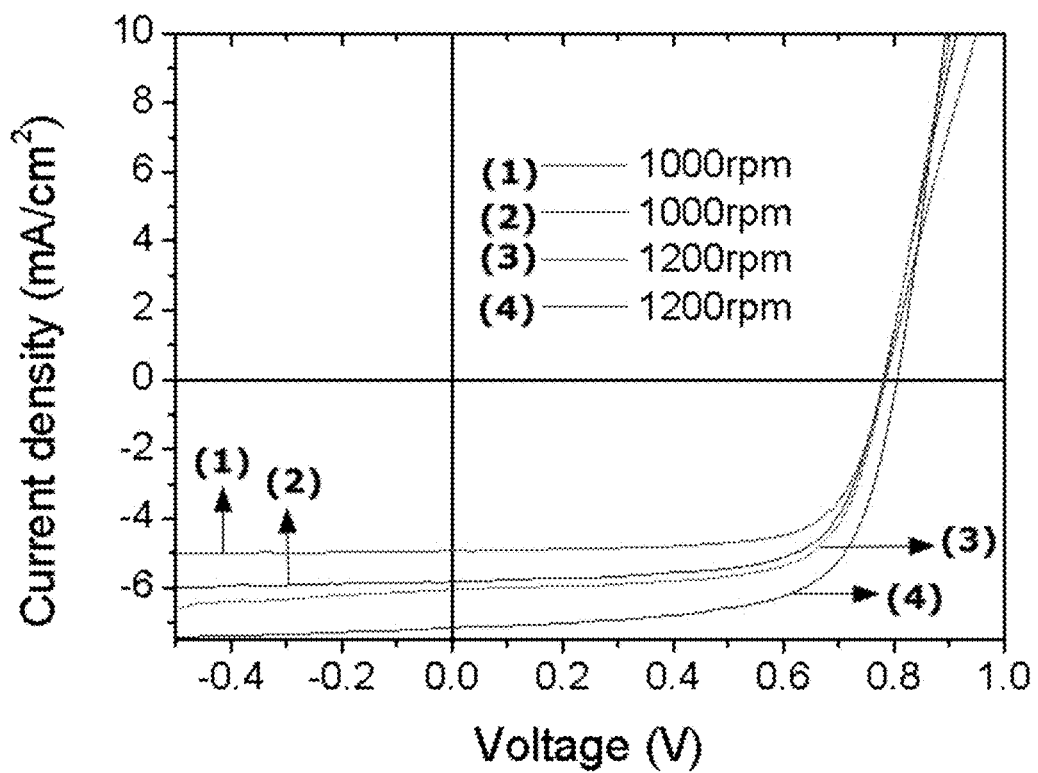

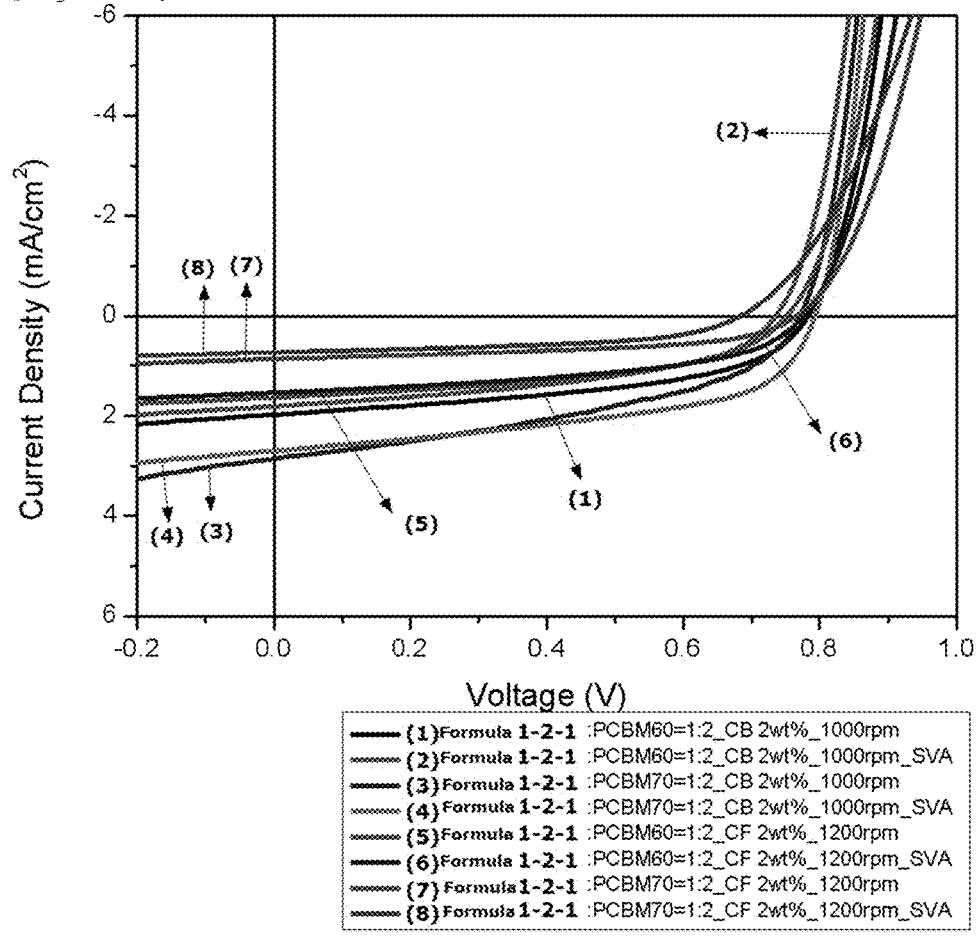

HETEROCYCLIC COMPOUND AND ORGANIC SOLAR CELL COMPRISING THE SAME

This application is a National Stage Entry of International Application No. PCT/KR2015/003608, filed Apr. 10, 2015, and claims the benefit of Korean Application No. 10-2014-0047209, filed on Apr. 21, 2014, all of which are hereby incorporated by reference in their entirety for all purposes as if fully set forth herein.

TECHNICAL FIELD

The present specification relates to a heterocyclic compound and an organic solar cell including the same.

BACKGROUND ART

An organic solar cell is a device that may directly convert solar energy into electric energy by applying a photovoltaic effect. A solar cell may be divided into an inorganic solar cell and an organic solar cell, depending on the materials constituting a thin film. Typical solar cells are made through a p-n junction by doping crystalline silicon (Si), which is an inorganic semiconductor. Electrons and holes generated by absorbing light diffuse to p-n junction points and move to an electrode while being accelerated by the electric field. The power conversion efficiency in this process is defined as the ratio of electric power given to an external circuit and solar power entering the solar cell, and the efficiency have reached approximately 24% when measured under a currently standardized virtual solar irradiation condition. However, since inorganic solar cells in the related art already have shown the limitation in economic feasibility and material demands and supplies, an organic semiconductor solar cell, which is easily processed and inexpensive and has various functionalities, has come into the spotlight as a long-term alternative energy source.

For the solar cell, it is important to increase efficiency so as to output as much electric energy as possible from solar energy. In order to increase the efficiency of this solar cell, it is important to generate as many excitons as possible inside a semiconductor, but it is also important to pull the generated charges to the outside without loss. One of the reasons for the charge loss is the dissipation of generated electrons and holes due to recombination. Various methods have been proposed to deliver generated electrons and holes to an electrode without loss, but additional processes are required in most cases and accordingly, manufacturing costs may be increased.

CITATION LIST

Patent Document

U.S. Pat. No. 5,331,183
U.S. Pat. No. 5,454,880

DETAILED DESCRIPTION OF THE INVENTION

Technical Problem

An object of the present specification is to provide a heterocyclic compound and an organic solar cell including the same.

Technical Solution

The present specification provides a heterocyclic compound represented by the following Formula 1.

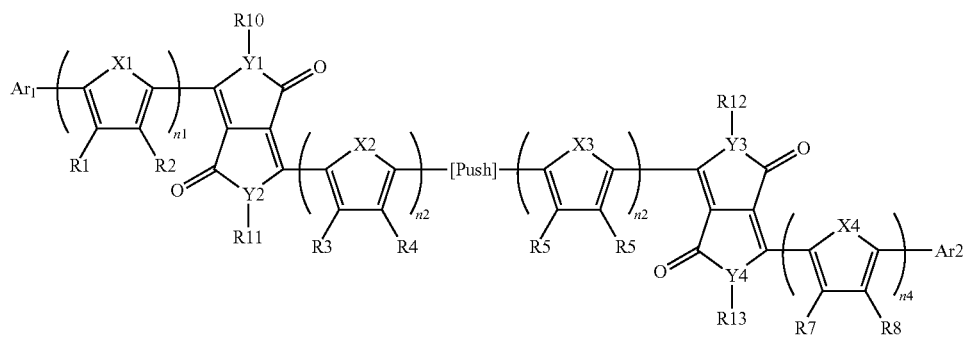

[Formula 1]

In Formula 1, n1 to n4 are each an integer of 1 to 3, when n1 to n4 are each 2 or more, two or more structures in the parenthesis are the same as or different from each other, X1 to X4 are the same as or different from each other, and are each independently CRR', NR, O, SiRR', PR, S, GeRR', Se, or Te, Y1 to Y4 are the same as or different from each other, and each independently CR", N, SiR", P, or GeR", R, R', R", R1 to R8, and R10 to R13 are the same as or different from each other, and are each independently hydrogen; deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; and a substituted or unsubstituted heterocyclic group,

[Push] has a structure which acts as an electron donor, and the structure is one of the following structures,

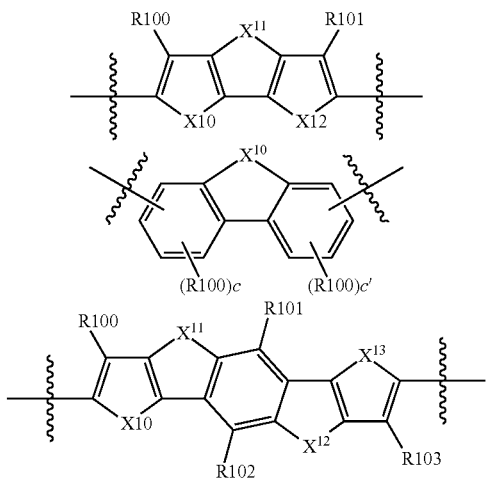

c and c' are each an integer of 1 to 3, when c is 2 or more, two or more R100's are the same as or different from each other, when c' is 2 or more, two or more R101's are the same as or different from each other, and X10 to X13 are the same as or different from each other, and are each independently CRaRb, NRa, O, SiRaRb, PRa, S, GeRaRb, Se, or Te, Ra, Rb, and R100 to R103 are the same as or different from each other, and are each independently hydrogen; deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group, Ar1 and Ar2 are the same as or different from each other, and are each independently any one of the following structures,

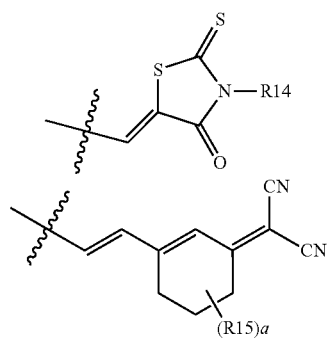

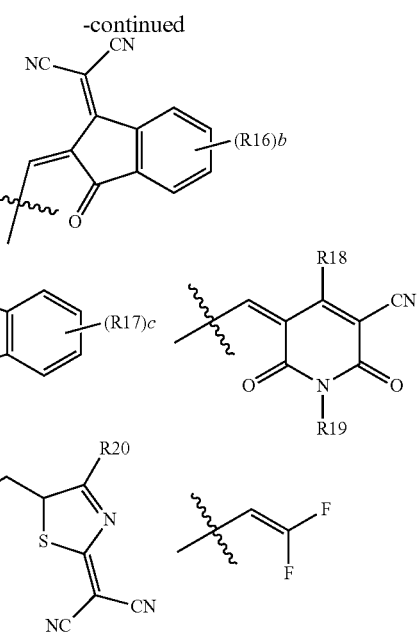

in the structures, a is an integer of 1 to 7, b and c are each an integer of 1 to 4, when a is 2 or more, two or more R15's are the same as or different from each other, when b is 2 or more, two or more R16's are the same as or different from each other, and when c is 2 or more, two or more R17's are the same as or different from each other, and R14 to R20 are the same as or different from each other, and are each independently hydrogen; deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group.

Further, the present specification provides an organic solar cell including: a first electrode; a second electrode provided to face the first electrode; and one or more organic material layers provided between the first electrode and the second electrode and including a photoactive layer, in which one or more layers of the organic material layers include the above-described heterocyclic compound.

Advantageous Effects

A heterocyclic compound according to an exemplary embodiment of the present specification includes [Push] having electron donor properties and Ar1 and Ar2 relatively having electron withdrawing properties. Further, the heterocyclic compound may include a linker which has excellent planarity and links the [Push] and Ar1 or A2, and thus, allow excitons formed to rapidly move in the molecule, thereby maximizing polarization of the excitons, and having low band gap characteristics.

In addition, since the heterocyclic compound according to an exemplary embodiment of the present specification has excellent crystallinity, it may be expected to increase the fill factor (FF).

Accordingly, the heterocyclic compound may be used as a material for an organic material layer of an organic solar cell, and an organic solar cell including the same may exhibit characteristics which are excellent in an increase in open-circuit voltage and short-circuit current and/or an increase in efficiency, and the like.

The heterocyclic compound according to an exemplary embodiment of the present specification may be used either alone or in mixture with other materials in an organic solar cell, and it may be expected to improve the efficiency, and improve the service life of a device by characteristics such as thermal stability of the compound.

BRIEF DESCRIPTION OF DRAWINGS

FIG. 1 is a view illustrating an organic solar cell according to an exemplary embodiment of the present specification.

FIG. 2 is a view illustrating the NMR data of Formula 1-1-1.

FIG. 3 is a view illustrating the MS spectrum of Formula 1-1-1.

FIG. 4 is a view illustrating the MS spectrum of Formula 1-1-2.

FIG. 5 is a view illustrating the differential scanning calorimetry (DSC) of Formula 1-1-2.

FIG. 6 is a view illustrating the NMR graph of Formula 1-1-2.

FIG. 7 is a view illustrating absorption spectra of Comparative Example 1 in a solution state and Formula 1-1-2.

FIG. 8 is a view illustrating absorption spectra of Comparative Example 1 in a solid state and Formula 1-1-2.

FIG. 9 is a view illustrating the incident photon-to-current efficiency (IPCE) of the organic solar cell using Formula 1-1-2.

FIG. 10 is a view illustrating the MS spectrum of Formula 1-2-1.

FIG. 11 is a view illustrating the differential scanning calorimetry (DSC) of Formula 1-2-1.

FIG. 12 is a view illustrating the current density according to the voltage of the organic solar cell using Formula 1-1-2.

FIG. 13 is a view illustrating the current density according to the voltage of the organic solar cell using Formula 1-2-1.

EXPLANATION OF REFERENCE NUMERALS AND SYMBOLS

101: Substrate
102: First electrode
103: Hole transport layer
104: Photoactive layer
105: Second electrode

BEST MODE

Hereinafter, the present specification will be described in detail.

The present specification provides the heterocyclic compound represented by Formula 1.

In the present specification, ⫲ means a moiety which is linked to another substituent.

In an exemplary embodiment of the present specification, the [Push] acts as an electron donor in the heterocyclic compound.

In one exemplary embodiment, the [Push] has a highest occupied molecular orbital (HOMO) energy level of 5.0 eV to 6.0 eV.

In one exemplary embodiment, the [Push] has a band gap of 2 eV to 3.5 eV.

In the heterocyclic compound according to an exemplary embodiment of the present specification, [Push] relatively acts as an electron donor, and Ar1 and Ar2 act as an electron acceptor. In this case, electrons in the lowest unoccupied molecular orbital (LUMO) state are relatively localized in Ar1 and Ar2. This allows a polarization to be present between [Push] and Ar1 or Ar2.

The present specification may maximize localization of electrons by introducing a linker, which has relatively excellent planarity and has a conjugated structure (conjugation), between the [Push] and Ar1 or Ar2, to allow electrons to rapidly move in the direction of Ar1 or Ar2 in the compound. In this case, the excitons formed may rapidly move in the molecule, and polarization of the excitons may be maximized, thereby having low band gap characteristics.

In the present specification, the energy level means the size of energy. Accordingly, even when the energy level is expressed in the negative (−) direction from the vacuum level, it is interpreted that the energy level means an absolute value of the corresponding energy value. For example, the HOMO energy level means the distance from the vacuum level to the highest occupied molecular orbital. Further, the LUMO energy level means the distance from the vacuum level to the lowest unoccupied molecular orbital.

In this case, high current and high efficiency may be expected in a device such as an organic solar cell including the heterocyclic compound according to an exemplary embodiment of the present specification.

In an exemplary embodiment of the present specification, R10 to R13 are the same as or different from each other, and are each independently a substituted or unsubstituted, straight-chained or branched alkyl group having 4 to 30 carbon atoms.

In this case, it is possible to induce a contact with an acceptor in Ar1 and Ar2 by minimizing a contact of the backbone of the heterocyclic compound with the acceptor. Through the contact of Ar1 and Ar2, in which electrons are relatively localized, with the acceptor, electrons in the device may easily move from an electron donor material (donor) to an electron accepting material (acceptor), thereby expecting high efficiency in the device.

In an exemplary embodiment of the present specification, the [Push] is

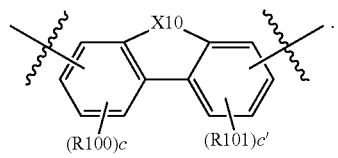

In another exemplary embodiment, the [Push] is

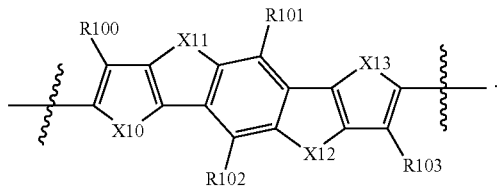

In an exemplary embodiment of the present specification, the heterocyclic compound represented by Formula 1 is represented by the following Formula 1-1 or 1-2.

tuted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group. Examples of the substituents will be described below, but are not limited thereto.

The term "substitution" means that a hydrogen atom bonded to a carbon atom of a compound is changed into another substituent, and a position to be substituted is not limited as long as the position is a position at which the

[Formula 1-1]

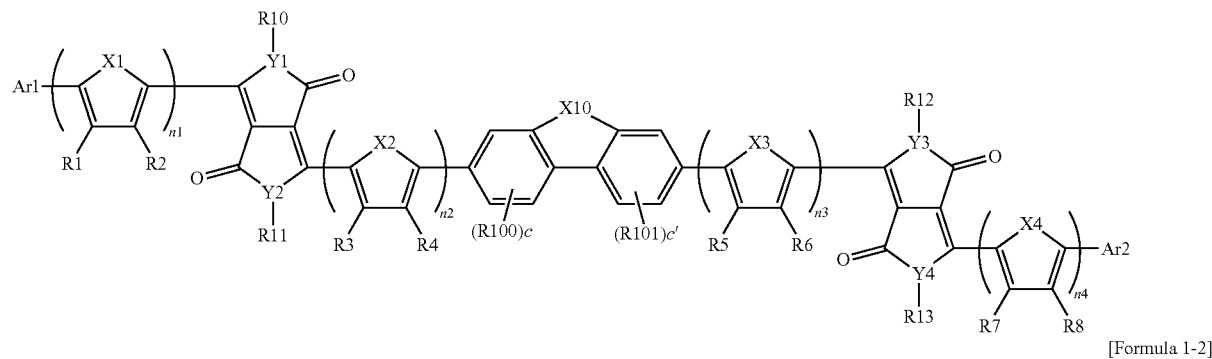

[Formula 1-2]

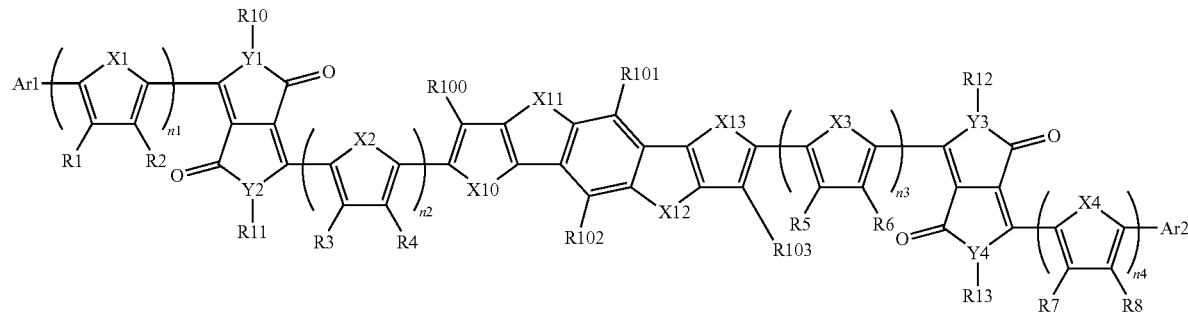

In Formulae 1-1 and 1-2, n1 to n4, X1 to X4, Y1 to Y4, R1 to R8, R10 to R13, Ar1, and Ar2 are the same as those defined in Formula 1, c and c' are each an integer of 1 to 3, when c is 2 or more, two or more R100's are the same as or different from each other, when c' is 2 or more, two or more R101's are the same as or different from each other, and X10 to X13 are the same as or different from each other, and are each independently CRaRb, NRa, O, SiRaRb, PRa, S, GeRaRb, Se, or Te, and Ra, Rb, and R100 to R103 are the same as or different from each other, and are each independently hydrogen; deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstihydrogen atom is substituted, that is, a position at which the substituent may be substituted, and when two or more are substituted, the two or more substituents may be the same as or different from each other.

The term "substituted or unsubstituted" as used herein means being substituted with one or more substituents selected from the group consisting of deuterium; a halogen group; an alkyl group; an alkenyl group; an alkoxy group; an ester group; a carbonyl group; a carboxyl group; a hydroxyl group; a cycloalkyl group; a silyl group; an arylalkenyl group; an aryloxy group; an alkylthioxy group; an alkylsulfoxy group; an arylsulfoxy group; a boron group; an alkylamine group; an aralkylamine group; an arylamine group; a heterocyclic group; an arylamine group; an aryl group; a nitrile group; a nitro group; a hydroxyl group; and a heterocyclic group, or having no substituent.

The substituents may be unsubstituted or substituted with an additional substituent.

In the present specification, the halogen group may be fluorine, chlorine, bromine, or iodine.

In the present specification, the number of carbon atoms of the imide group is not particularly limited, but is preferably 1 to 25. Specifically, the imide group may be a compound having the following structure, but is not limited thereto.

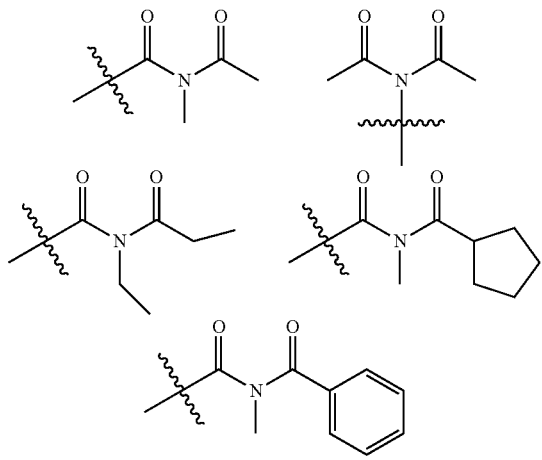

In the present specification, for the amide group, one or two nitrogen of the amide group may be substituted with hydrogen, a straight-chained, branched, or cyclic alkyl group having 1 to 25 carbon atoms, or an aryl group having 6 to 25 carbon atoms. Specifically, the amide group may be a compound having the following structural formula, but is not limited thereto.

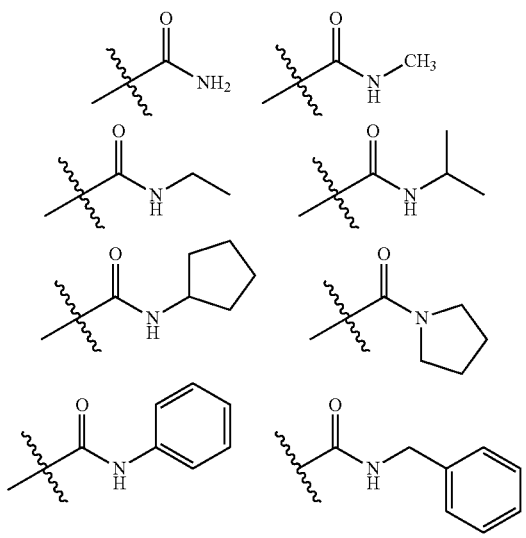

In the present specification, the alkyl group may be straight-chained or branched, and the number of carbon atoms thereof is not particularly limited, but is preferably 1 to 50. Specific examples thereof include methyl, ethyl, propyl, n-propyl, isopropyl, butyl, n-butyl, isobutyl, tert-butyl, sec-butyl, 1-methyl-butyl, 1-ethylbutyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, the cycloalkyl group is not particularly limited, but is preferably a cycloalkyl group having 3 to 60 carbon atoms, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group may be straight-chained, branched, or cyclic. The number of carbon atoms of the alkoxy group is not particularly limited, but is preferably 1 to 20. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, the alkenyl group may be straight-chained or branched, and the number of carbon atoms thereof is not particularly limited, but is preferably 2 to 40. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, specific examples of the silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, the aryl group may be a monocyclic aryl group or a polycyclic aryl group, and includes the case where an alkyl group having 1 to 25 carbon atoms or an alkoxy group having 1 to 25 carbon atoms is substituted. Further, the aryl group in the present specification may mean an aromatic ring.

When the aryl group is a monocyclic aryl group, the number of carbon atoms thereof is not particularly limited, but is preferably 6 to 25. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 24. Specific examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, the fluorenyl group has a structure in which two cyclic organic compounds are linked to each other through one atom.

In the present specification, the fluorenyl group may be substituted, and adjacent substituents may combine with each other to form a ring.

When the fluorenyl group is substituted, the fluorenyl group may be

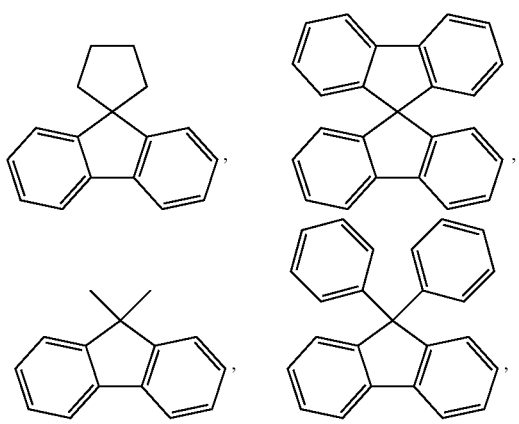

and the like. However, the fluorenyl group is not limited thereto.

In the present specification, a heterocyclic group is a heterocyclic group including one or more of O, N, and S as a hetero element, and the number of carbon atoms thereof is not particularly limited, but is preferably 2 to 60. Examples of the heterocyclic group include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

The heterocyclic group may be monocyclic or polycyclic, and may be an aromatic ring, an aliphatic ring, or a condensed ring of the aromatic ring and the aliphatic ring.

In the present specification, examples of the arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group including two or more aryl groups may include a monocyclic aryl group, a polycyclic aryl group, or both a monocyclic aryl group and a polycyclic aryl group.

Specific examples of the arylamine group include phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamine group, a phenylnaphthylamine group, a ditolylamine group, a phenyltolylamine group, carbazole, a triphenylamine group, and the like, but are not limited thereto.

In the present specification, the heteroaryl group in the heteroarylamine group may be selected from the above-described examples of the heterocyclic group.

In the present specification, the aryl group in the aryloxy group, the arylthioxy group, the arylsulfoxy group, and the aralkylamine group is the same as the above-described examples of the aryl group. Specifically, examples of the aryloxy group include phenoxy, p-tolyloxy, m-tolyloxy, 3,5-dimethyl-phenoxy, 2,4,6-trimethylphenoxy, p-tert-butylphenoxy, 3-biphenyloxy, 4-biphenyloxy, 1-naphthyloxy, 2-naphthyloxy, 4-methyl-1-naphthyloxy, 5-methyl-2-naphthyloxy, 1-anthryloxy, 2-anthryloxy, 9-anthryloxy, 1-phenanthryloxy, 3-phenanthryloxy, 9-phenanthryloxy, and the like, examples of the arylthioxy group include a phenylthioxy group, a 2-methylphenylthioxy group, a 4-tert-butylphenylthioxy group, and the like, and examples of the arylsulfoxy group include a benzenesulfoxy group, a p-toluenesulfoxy group, and the like, but are not limited thereto.

In the present specification, the alkyl group in the alkylthioxy group and the alkylsulfoxy group is the same as the above-described examples of the alkyl group. Specifically, examples of the alkylthioxy group include a methylthioxy group, an ethylthioxy group, a tert-butylthioxy group, a hexylthioxy group, an octylthioxy group, and the like, and examples of the alkylsulfoxy group include mesyl, an ethylsulfoxy group, a propylsulfoxy group, a butylsulfoxy group, and the like, but are not limited thereto.

In an exemplary embodiment of the present specification, X1 is S.

In another exemplary embodiment, X2 is S.

In an exemplary embodiment of the present specification, X3 is S.

In another exemplary embodiment, X4 is S. In an exemplary embodiment of the present specification, n1 is 2.

In another exemplary embodiment, n2 is 1.

In an exemplary embodiment of the present specification, n3 is 1.

In another exemplary embodiment, n4 is 2.

In an exemplary embodiment of the present specification, R1 is hydrogen.

In another exemplary embodiment of the present specification, R2 is hydrogen.

In another exemplary embodiment, R4 is hydrogen. In an exemplary embodiment of the present specification, R5 is hydrogen.

In another exemplary embodiment, R6 is hydrogen. In an exemplary embodiment of the present specification, R7 is hydrogen.

In an exemplary embodiment of the present specification, R8 is hydrogen.

In an exemplary embodiment of the present specification, Y1 is N.

In another exemplary embodiment of the present specification, Y2 is N.

In another exemplary embodiment, Y3 is N.

In an exemplary embodiment of the present specification, Y4 is N.

In an exemplary embodiment of the present specification, Ar1 is

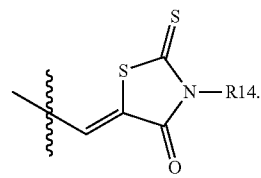

In an exemplary embodiment of the present specification, Ar2 is

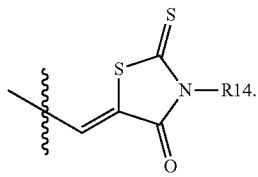

In an exemplary embodiment of the present specification, X1 to X4 are S, Y1 and Y4 is N, Ar1 and Ar2 are the same as or different from each other, and are each independently

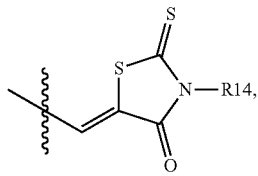

R10 to R13 are the same as or different from each other, and are each independently a substituted or unsubstituted, straight-chained or branched alkyl group having 6 to 16 carbon atoms, and R14 is a substituted or unsubstituted alkyl group having 1 to 16 carbon atoms.

In an exemplary embodiment of the present specification, R14 is a substituted or unsubstituted alkyl group.

In another exemplary embodiment, R14 is a straight-chained or branched alkyl group having 2 to 16 carbon atoms.

In still another exemplary embodiment, R14 is an ethyl group.

In an exemplary embodiment of the present specification, R10 is a substituted or unsubstituted alkyl group.

In another exemplary embodiment, R10 is a substituted or unsubstituted, branched alkyl group.

In still another exemplary embodiment, R10 is a substituted or unsubstituted 2-ethylhexyl group.

In an exemplary embodiment of the present specification, R10 is a 2-ethylhexyl group.

In an exemplary embodiment of the present specification, R11 is a substituted or unsubstituted alkyl group.

In another exemplary embodiment, R11 is a substituted or unsubstituted, branched alkyl group.

In still another exemplary embodiment, R11 is a substituted or unsubstituted 2-ethylhexyl group.

In an exemplary embodiment of the present specification, R11 is a 2-ethylhexyl group.

In an exemplary embodiment of the present specification, R12 is a substituted or unsubstituted alkyl group.

In another exemplary embodiment, R12 is a substituted or unsubstituted, branched alkyl group.

In still another exemplary embodiment, R12 is a substituted or unsubstituted 2-ethylhexyl group.

In an exemplary embodiment of the present specification, R12 is a 2-ethylhexyl group.

In an exemplary embodiment of the present specification, R13 is a substituted or unsubstituted alkyl group.

In another exemplary embodiment, R13 is a substituted or unsubstituted, branched alkyl group.

In still another exemplary embodiment, R13 is a substituted or unsubstituted 2-ethylhexyl group.

In an exemplary embodiment of the present specification, R13 is a 2-ethylhexyl group.

In an exemplary embodiment of the present specification, R100 is hydrogen.

In one exemplary embodiment, R101 is hydrogen.

In another exemplary embodiment, R102 is hydrogen.

In another exemplary embodiment, R103 is hydrogen.

In an exemplary embodiment of the present specification, X10 is S.

In another exemplary embodiment of the present specification, X10 is NRa.

In still another exemplary embodiment, X11 is S.

In yet another exemplary embodiment, X11 is SiRaRb.

In one exemplary embodiment, X12 is SiRaRb.

In another exemplary embodiment, X13 is S.

In one exemplary embodiment, Ra and Rb are the same as or different from each other, and are each independently a substituted or unsubstituted alkyl group; a substituted or unsubstituted alkoxy group; a substituted or unsubstituted aryl group; or a substituted or unsubstituted heterocyclic group.

In an exemplary embodiment of the present specification, Ra is a substituted or unsubstituted alkyl group.

In an exemplary embodiment of the present specification, Ra is a substituted or unsubstituted alkyl group having 1 to 30 carbon atoms.

In one exemplary embodiment, Ra is a substituted or unsubstituted octyl group.

In another exemplary embodiment, Ra is an octyl group.

In another exemplary embodiment of the present specification, Ra is a substituted or unsubstituted 1-octylnonyl group.

In one exemplary embodiment, Ra is a 1-octylnonyl group.

In an exemplary embodiment of the present specification, Rb is a substituted or unsubstituted alkyl group.

In an exemplary embodiment of the present specification, Rb is a substituted or unsubstituted alkyl group having 1 to 30 carbon atoms.

In another exemplary embodiment of the present specification, Rb is a substituted or unsubstituted 1-octylnonyl group.

In one exemplary embodiment, Rb is a 1-octylnonyl group.

In one exemplary embodiment, Rb is a substituted or unsubstituted octyl group.

In another exemplary embodiment, Rb is an octyl group.

In an exemplary embodiment of the present specification, the heterocyclic compound represented by Formula 1 is represented by the following Formula 1-1-1 or 1-1-2.

[Formula 1-1-1]

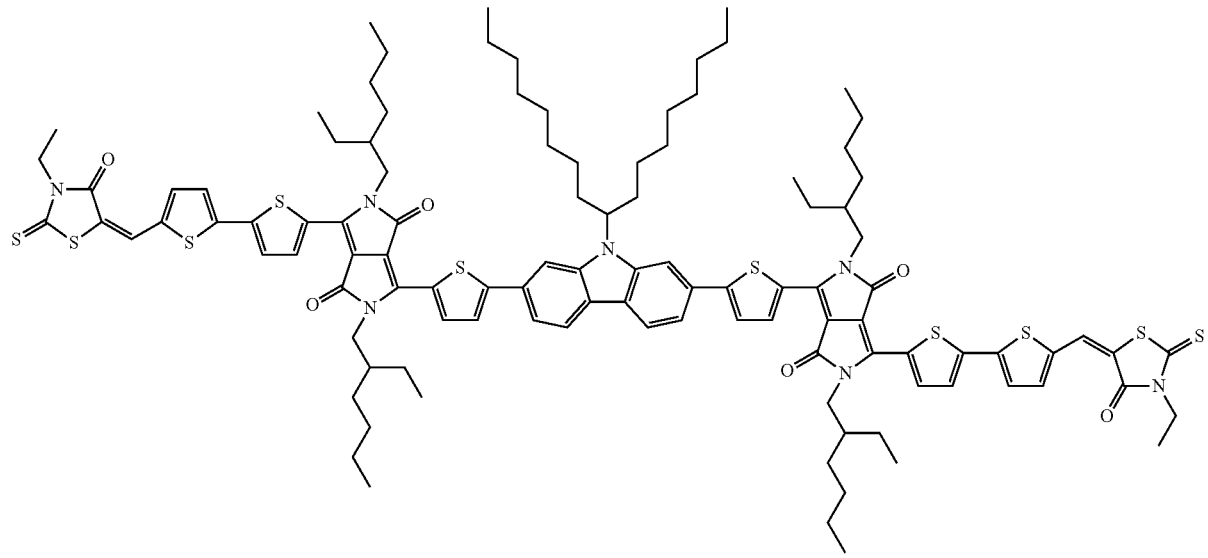

[Formula 1-1-2]

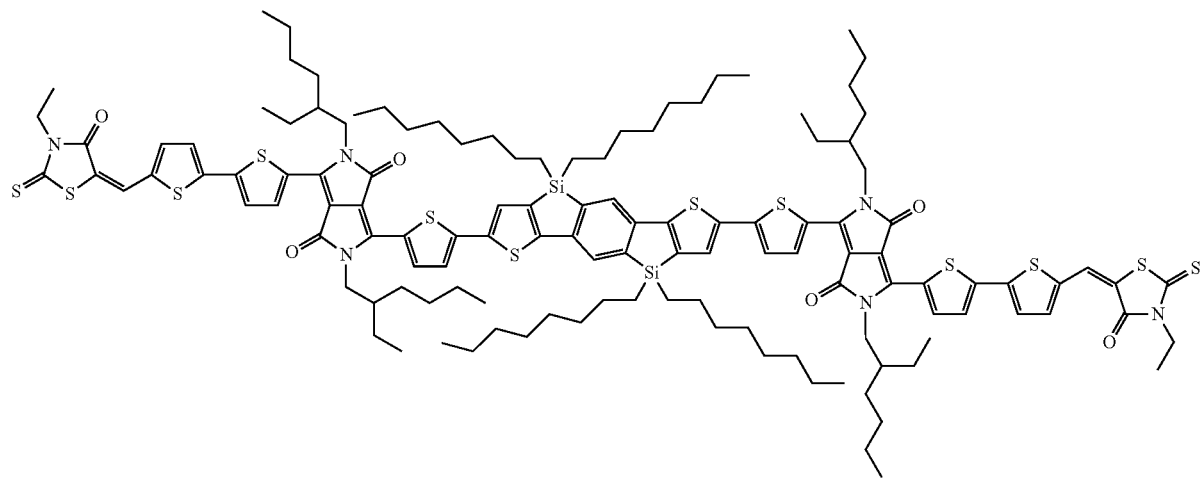

The heterocyclic compound may be prepared based on the Preparation Examples to be described below.

For the heterocyclic compound according to an exemplary embodiment of the present specification, a compound in which an aldehyde group is introduced into the end of a structure in the parenthesis of n1 and a halogen group is introduced into the end of a structure in the parenthesis of n2; a compound in which a halogen group is introduced into the end of a structure in the parenthesis of n3 and an aldehyde group is introduced into the end of a structure in the parenthesis of n4; and a compound in which an aldehyde group is introduced into each end by binding the [Push] thereto are prepared. Thereafter, not only a heterocyclic compound represented by Formula 1-1-1 or 1-1-2, but also a heterocyclic compound represented by Formula 1 may be prepared by introducing Ar1 and Ar2 thereinto.

The heterocyclic compound according to the present specification may be prepared by a multi-step chemical reaction. Monomers are prepared through an alkylation reaction, a Grignard reaction, a Suzuki coupling reaction, a Stille coupling reaction, and the like, and then final heterocyclic compounds may be prepared through a carbon-carbon coupling reaction such as a Stille coupling reaction. When the substituent to be introduced is a boronic acid or boronic ester compound, the final heterocyclic compounds may be prepared through a Suzuki coupling reaction, and when the substituent to be introduced is a tributyltin or trimethyltin compound, the final heterocyclic compounds may be prepared through a Stille coupling reaction, but the method is not limited thereto.

An exemplary embodiment of the present specification provides an organic solar cell including: a first electrode; a second electrode provided to face the first electrode; and one or more organic material layers provided between the first electrode and the second electrode and including a photoactive layer, in which one or more layers of the organic material layers include the heterocyclic compound.

The organic solar cell according to an exemplary embodiment of the present specification includes a first electrode, a photoactive layer, and a second electrode. The organic solar cell may further include a substrate, a hole transport layer, and/or an electron transport layer.

In an exemplary embodiment of the present specification, when the organic solar cell accepts a photon from an external light source, an electron and a hole are generated between an electron donor and an electron acceptor. The generated hole is transported to a positive electrode through an electron donor layer.

In an exemplary embodiment of the present specification, the organic material layer includes a hole transport layer, a hole injection layer, or a layer which simultaneously transports and injects holes, and the hole transport layer, the hole injection layer, or the layer which simultaneously transports and injects holes includes the heterocyclic compound.

In another exemplary embodiment, the organic material layer includes an electron injection layer, an electron transport layer, or a layer which simultaneously injects and transports electrons, and the electron injection layer, the electron transport layer, or the layer which simultaneously injects and transports electrons includes the heterocyclic compound.

FIG. 1 is a view illustrating an organic solar cell according to an exemplary embodiment of the present specification.

In an exemplary embodiment of the present specification, when the organic solar cell accepts a photon from an external light source, an electron and a hole are generated between an electron donor and an electron acceptor. The generated hole is transported to a positive electrode through an electron donor layer.

In an exemplary embodiment of the present specification, the organic solar cell may further include an additional organic material layer. The organic solar cell may reduce the number of organic material layers therein by using an organic material which simultaneously has various functions.

In an exemplary embodiment of the present specification, the first electrode is an anode, and the second electrode is a cathode. In another exemplary embodiment, the first electrode is a cathode, and the second electrode is an anode.

In an exemplary embodiment of the present specification, in the organic solar cell, a cathode, a photoactive layer, and an anode may be arranged in this order, and an anode, a photoactive layer, and a cathode may be arranged in this order, but the arrangement order is not limited thereto.

In another exemplary embodiment, in the organic solar cell, the anode, the hole transport layer, the photoactive layer, the electron transport layer, and the cathode may also be arranged in this order, and the cathode, the electron transport layer, the photoactive layer, the hole transport layer, and the anode may also be arranged in this order, but the arrangement order is not limited thereto.

In an exemplary embodiment of the present specification, the organic solar cell has a normal structure. In the normal structure, a substrate, an anode, an organic material layer including a photoactive layer, and a cathode may be stacked in this order.

In an exemplary embodiment of the present specification, the organic solar cell has an inverted structure. In the inverted structure, a substrate, a cathode, an organic material layer including a photoactive layer, and an anode may be stacked in this order. In an exemplary embodiment of the present specification, the organic solar cell has a tandem structure.

The organic solar cell according to an exemplary embodiment of the present specification may have one or two or more photoactive layers. The tandem structure may include two or more photoactive layers.

In another exemplary embodiment, a buffer layer may be provided between the photoactive layer and the hole transport layer, or between the photoactive layer and the electron transport layer. In this case, a hole injection layer may be further provided between the anode and the hole transport layer. Further, an electron injection layer may be further provided between the cathode and the electron transport layer.

In an exemplary embodiment of the present specification, the photoactive layer includes one or two or more selected from the group consisting of an electron donor and an electron acceptor, and the electron donor material includes the heterocyclic compound.

In an exemplary embodiment of the present specification, the electron acceptor material may be selected from the group consisting of fullerene, fullerene derivatives, bathocuproine, semi-conducting elements, semi-conducting compounds, and combinations thereof.

Specifically, the electron acceptor material is one or two or more compounds selected from the group consisting of fullerene, fullerene derivatives ((6,6)-phenyl-C61-butyric acid-methylester (PCBM) or (6,6)-phenyl-C61-butyric acid-cholesteryl ester (PCBCR)), perylene, polybenzimidazole (PBI), and 3,4,9,10-perylene-tetracarboxylic bis-benzimidazole (PTCBI).

In an exemplary embodiment of the present specification, the electron donor and the electron acceptor constitute a bulk heterojunction (BHJ).

The bulk heterojunction means that an electron donor material and an electron acceptor material are mixed with each other in a photoactive layer.

In an exemplary embodiment of the present specification, the photoactive layer has a bilayer thin film structure including an n-type organic material layer and a p-type organic material layer, and the p-type organic material layer includes the heterocyclic compound.

In the present specification, the substrate may be a glass substrate or a transparent plastic substrate having excellent transparency, surface smoothness, handleability, and waterproofing properties, but is not limited thereto, and the substrate is not limited as long as the substrate is typically used in the organic solar cell. Specific examples thereof include glass or polyethylene terephthalate (PET), polyethylene naphthalate (PEN), polypropylene (PP), polyimide (PI), triacetyl cellulose (TAC), and the like, but are not limited thereto.

The anode electrode may be made of a material which is transparent and has excellent conductivity, but is not limited thereto. Examples of the material include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or SnO2:Sb; an electrically conductive polymer, such as poly(3-methylthiophene), poly[3,4-(ethylene-1,2-dioxy)thiophene] (PEDT), polypyrrole, and polyaniline, and the like, but are not limited thereto.

A method of forming the anode electrode is not particularly limited, but the anode electrode may be formed, for example, by being applied onto one surface of a substrate using sputtering, e-beam, thermal deposition, spin coating, screen printing, inkjet printing, doctor blade, or a gravure printing method, or by being coated in the form of a film.

When the anode electrode is formed on a substrate, the anode electrode may be subjected to processes of cleaning, removing moisture, and hydrophilic modification.

For example, a patterned ITO substrate is sequentially cleaned with a cleaning agent, acetone, and isopropyl alcohol (IPA), and then dried on a hot plate at 100 to 150° C. for 1 to 30 minutes, preferably at 120° C. for 10 minutes in order to remove moisture, and when the substrate is completely cleaned, the surface of the substrate is hydrophilically modified.

Through the surface modification as described above, the junction surface potential may be maintained at a level suitable for a surface potential of a photoactive layer. Further, during the modification, a polymer thin film may be easily formed on an anode electrode, and the quality of the thin film may also be improved.

Examples of a pre-treatment technology for an anode electrode include a) a surface oxidation method using a parallel flat plate-type discharge, b) a method of oxidizing the surface through ozone produced by using UV (ultraviolet) rays in a vacuum state, c) an oxidation method using oxygen radicals produced by plasma, and the like.

One of the methods may be selected depending on the state of the anode electrode or the substrate. However, even though any method is used, it is preferred to commonly prevent oxygen from being separated from the surface of the anode electrode or the substrate, and maximally inhibit moisture and organic materials from remaining. In this case, it is possible to maximize a substantial effect of the pre-treatment.

As a specific example, it is possible to use a method of oxidizing the surface through ozone produced by using UV. In this case, a patterned ITO substrate after being ultrasonically cleaned is baked on a hot plate and dried well, and then introduced into a chamber, and the ITO substrate patterned may be cleaned by ozone generated by reacting an oxygen gas with UV light by operating a UV lamp.

However, the surface modification method of the ITO substrate patterned in the present specification needs not be particularly limited, and any method may be used as long as the method is a method of oxidizing a substrate.

The cathode electrode may be a metal having a low work function, but is not limited thereto. Specific examples thereof include: a metal, such as magnesium, calcium, sodium, potassium, titanium, indium, yttrium, lithium, gadolinium, aluminum, silver, tin, and lead, or alloys thereof; and a multi-layered material, such as LiF/Al, $LiO_2$/Al, LiF/Fe, Al:Li, Al:$BaF_2$, and Al:$BaF_2$:Ba, but are not limited thereto.

The cathode electrode may be deposited and formed in a thermal evaporator showing a vacuum degree of $5\times10^{-7}$ torr or less, but the forming method is not limited to this method.

The hole transport layer and/or electron transport layer materials serve to efficiently transfer electrons and holes separated from a photoactive layer to the electrode, and the materials are not particularly limited.

The hole transport layer material may be poly(3,4-ethylenediocythiophene) doped with poly(styrenesulfonic acid) (PEDOT:PSS) and molybdenum oxide ($MoO_x$); vanadium oxide ($V_2O_5$); nickel oxide (NiO); and tungsten oxide ($WO_x$), and the like, but is not limited thereto.

The electron transport layer material may be electron-extracting metal oxides, and specific examples thereof include: a metal complex of 8-hydroxyquinoline; a complex including $Alq_3$; a metal complex including Liq; LiF; Ca; titanium oxide ($TiO_x$); zinc oxide (ZnO); and cesium carbonate ($Cs_2CO_3$), and the like, but are not limited thereto.

The photoactive layer may be formed by dissolving a photoactive material such as an electron donor and/or an electron acceptor in an organic solvent, and then applying the solution by a method such as spin coating, dip coating, screen printing, spray coating, doctor blade, and brush painting, but the forming method is not limited thereto.

A preparation method of the heterocyclic compound and the manufacture of an organic solar cell including the same will be described in detail in the following Preparation Examples and Examples. However, the following Examples are provided for exemplifying the present specification, and the scope of the present specification is not limited thereby.

Preparation Example 1. Preparation of Formula A

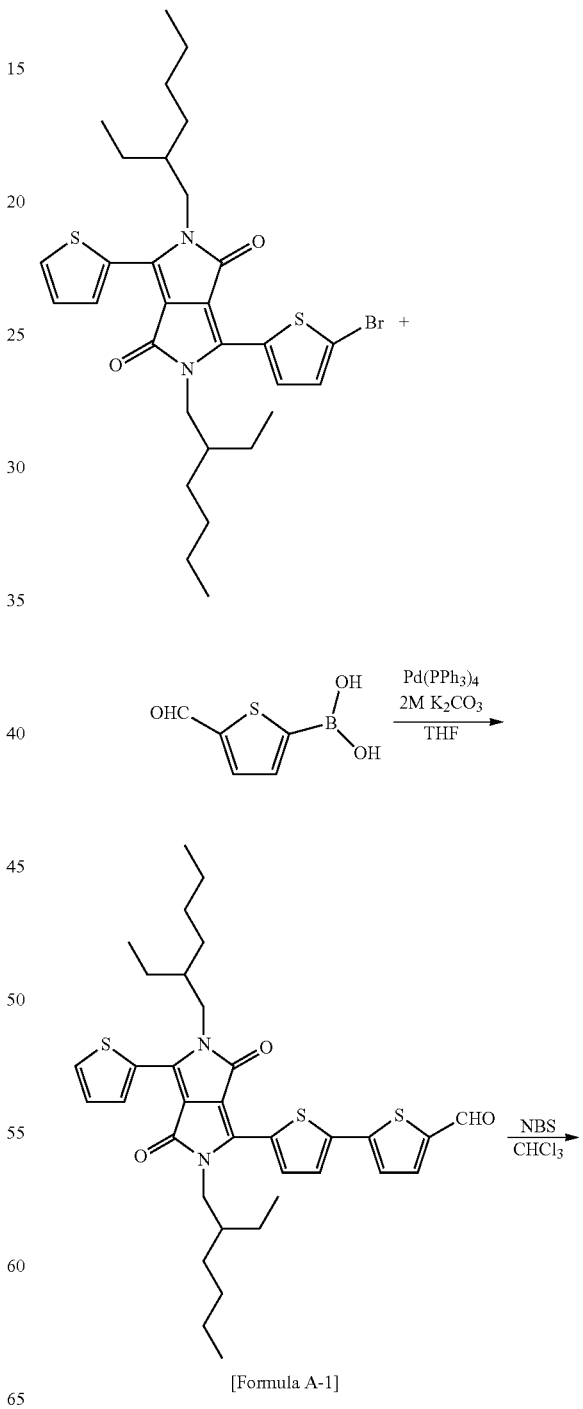

[Formula A-1]

-continued

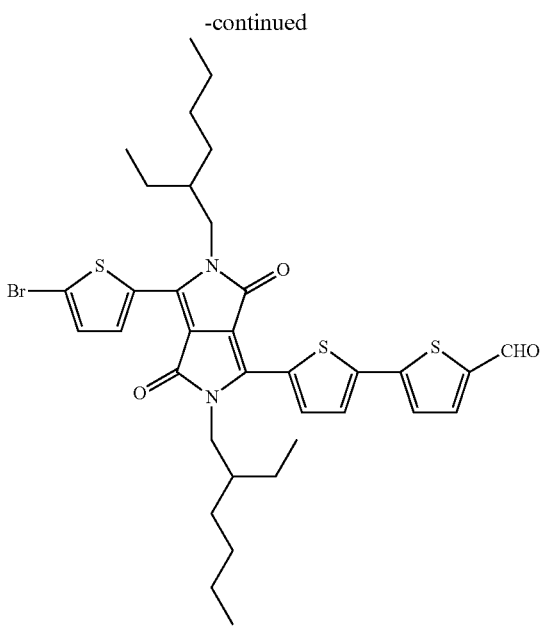

[Formual A]

(1) 3-(5-bromothiophen-2-yl)-2,5-bis(2-ethylhexyl)-6-(thiophen-2-yl)pyrrolo[3,4-c]pyrrole-1,4(2H,5H)-dione (Br-DPP) (6.0 g, 10 mmol) and 2-aldehyde-thiophene boronic ester (2.65 g, 17 mmol) were dissolved in 300 mL of tetrahydrofuran (THF), a Pd(PPh$_3$)$_4$ catalyst (0.347 g, 0.3 mmol) was added thereto, and the resulting solution was stirred at 70° C. for 72 hours. After the reaction was performed, an extraction was performed with dichloromethane (DCM), the remaining water was removed over magnesium sulfate (MgSO$_4$), and then the solvent was removed under reduced pressure. A dark purple solid Formula A-1 was obtained by subjecting the remaining product to silica column (eluent: hexane/DCM gradient=10:1 to 1:1).

(2) Formula A-1 (5.54 g, 8.73 mmol) was dissolved in 200 mL of chloroform (CHCl$_3$), N-bromosuccinimide (NBS) (1.864 g, 10.47 mmol) was added thereto, and the resulting solution was stirred at normal temperature for 6 hours. After the reaction was performed, an extraction was performed with dichloromethane (DCM), the remaining water was removed over magnesium sulfate (MgSO$_4$), and then the solvent was removed under reduced pressure. A dark purple solid was obtained by subjecting the remaining product to silica column (eluent: hexane/DCM gradient=10:1 to 1:

Preparation Example 2. Preparation of Formula B

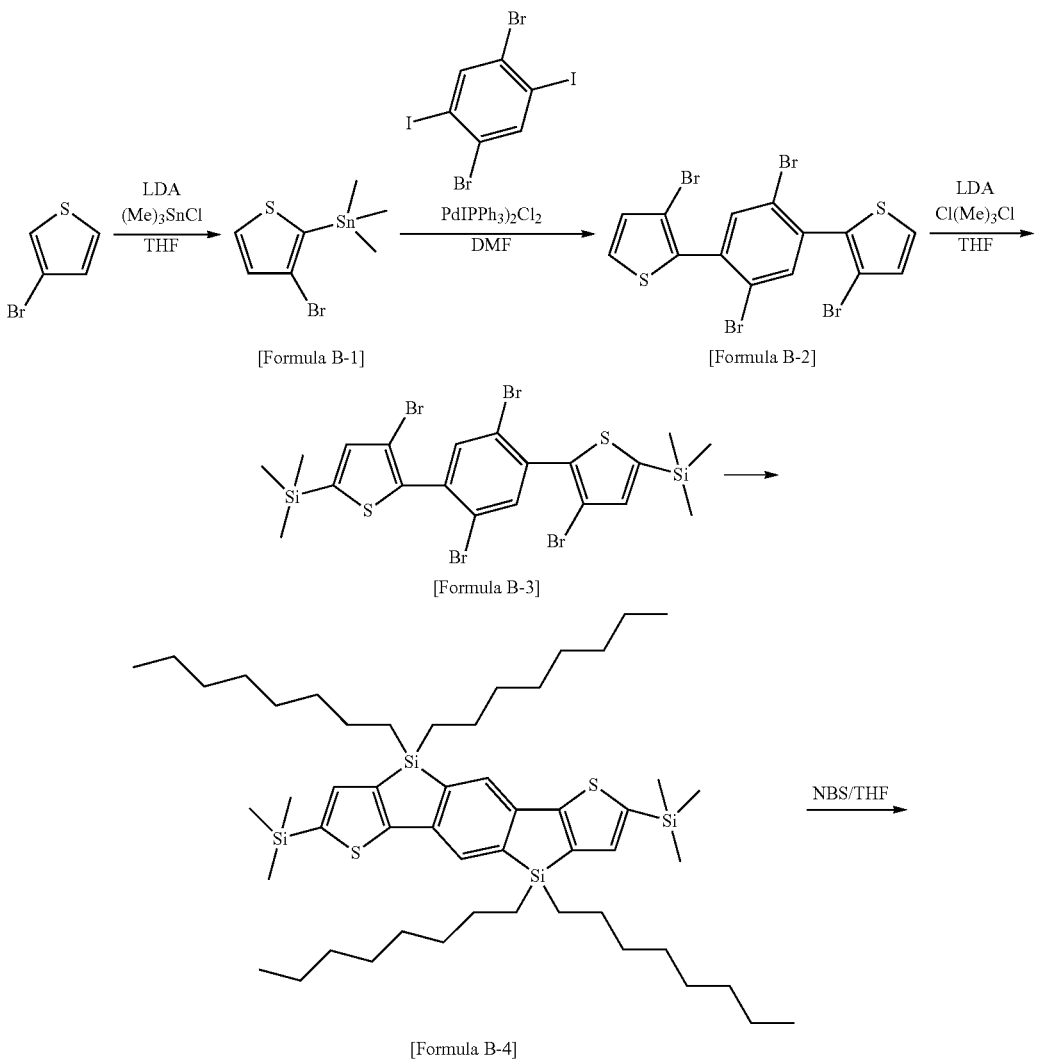

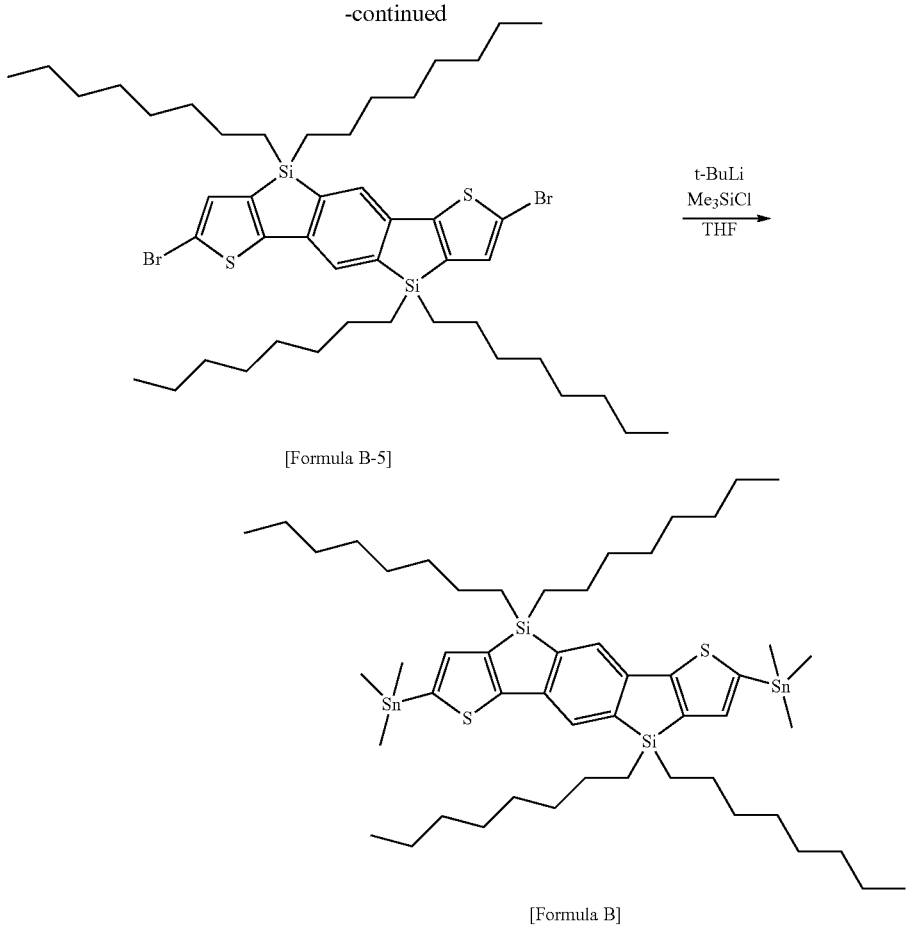

[Formula B-5]

[Formula B]

(1) 3-bromothiophene (10 g, 61.33 mmol) was dissolved in 100 mL of tetrahydrofuran (THF), 2.0 M lithium diisopropylamide (LDA) (31.25 mL, 62.5 mmol) was slowly injected thereinto at −78° C., and then the resulting solution was stirred at −60° C. for 30 minutes. Trimethyltinchloride (1 M, 63 mL, 63 mmol) was added thereto at −78° C., the resulting solution was stirred for 1 hour, and the temperature was slowly increased to normal temperature. The solution was extracted with dichloromethane (DCM), and then the remaining water was removed over magnesium sulfate (MgSO$_4$). A yellowish liquid Formula B-1 was obtained by removing the solvent from the remaining solution under reduced pressure.

(2) Bis-triphenylphosphine palladium (II) dichloride (Pd (PPh$_3$)$_2$Cl$_2$) and 1,4-dibromo-2,5-diiode-benzene (12.2 g, 25 mmol) were dissolved in 100 mL of dimethylformamide (DMF), and then the resulting solution was heated to 80° C. 2-trimethyltin-3-bromothiophene (18.7 g, 57.4 mmol) was injected into the solution, and the resulting solution was stirred at 120° C. for 40 hours. After the reaction was performed, the solvent was removed by extracting the solution with dichloromethane (DCM), and reducing pressure. A grey powder Formula B-2 was obtained by recrystallizing the remaining product with dichloromethane (DCM) and methanol (MeOH).

(3) Formula B-2 (9.48 g, 17 mmol) was dissolved in 300 mL of tetrahydrofuran (THF), 2.0 M lithium diisopropylamide (LDA) (19.5 mL, 39 mmol) was slowly injected thereinto at −78° C., and then the resulting solution was stirred at −60° C. for 1 hour. The temperature was reduced to −78° C., trimethylchlorosilane (5 mL, 39 mmol) was added thereto, the resulting solution was stirred for 1 hour, and then the temperature was slowly increased to normal temperature. After the solution was extracted with dichloromethane (DCM), the remaining water was removed over magnesium sulfate (MgSO$_4$), and then the solvent was removed under reduced pressure. A white solid Formula B-3 was obtained by recrystallizing the remaining product with 2-propanol.

(4) Formula B-3 (2 g, 2.85 mmol) was dissolved in 100 mL of tetrahydrofuran (THF), 1.7 M tertiary-butyl lithium (tert-BuLi) (15.3 mL, 26 mmol) was slowly injected thereinto at −78° C., and then the resulting solution was stirred at −78° C. for 2 hours. Dioctyldichlorosilane (3.05 mL, 8.83 mmol) was added thereto at the same temperature, and the temperature was slowly increased to normal temperature. After the solution was extracted with dichloromethane (DCM), the remaining water was removed over magnesium sulfate (MgSO$_4$), and then the solvent was removed under reduced pressure. A yellowish oil Formula B-4 was obtained by subjecting the remaining product to silica column (eluent: hexane).

(5) After B-4 (1.81 g, 2.03 mmol) was dissolved in 60 mL of tetrahydrofuran (THF), N-bromosuccinimide (NBS) (0.81 g, 4.6 mmol) was injected thereto at normal temperature, and then the resulting solution was stirred for 12 hours. After the reaction was performed, the solution was added to 100 mL of water, and an extraction was performed with dichloromethane (DCM). The remaining water was removed over magnesium sulfate (MgSO$_4$), and then the solvent was removed under reduced pressure. A yellowish oil Formula B-5 was obtained by subjecting the remaining product to silica column (eluent: hexane).

(6) Formula B-5 (0.87 g, 1.16 mmol) was dissolved in 60 mL of tetrahydrofuran (THF), 1.7 M tertiary-butyl lithium (tert-BuLi) (4.12 mL, 7 mmol) was slowly injected thereinto at −78° C., and then the resulting solution was stirred at −78° C. for 2 hours. 1M trimethyltinchloride (8 mL, 8 mmol) was added thereto at the same temperature, and the temperature was slowly increased to normal temperature. After the solution was extracted with dichloromethane (DCM), a yellowish oil Formula B was obtained by removing the remaining water over magnesium sulfate (MgSO$_4$), and then removing the solvent under reduced pressure.

Preparation Example 3. Preparation of Formula 1-1-1

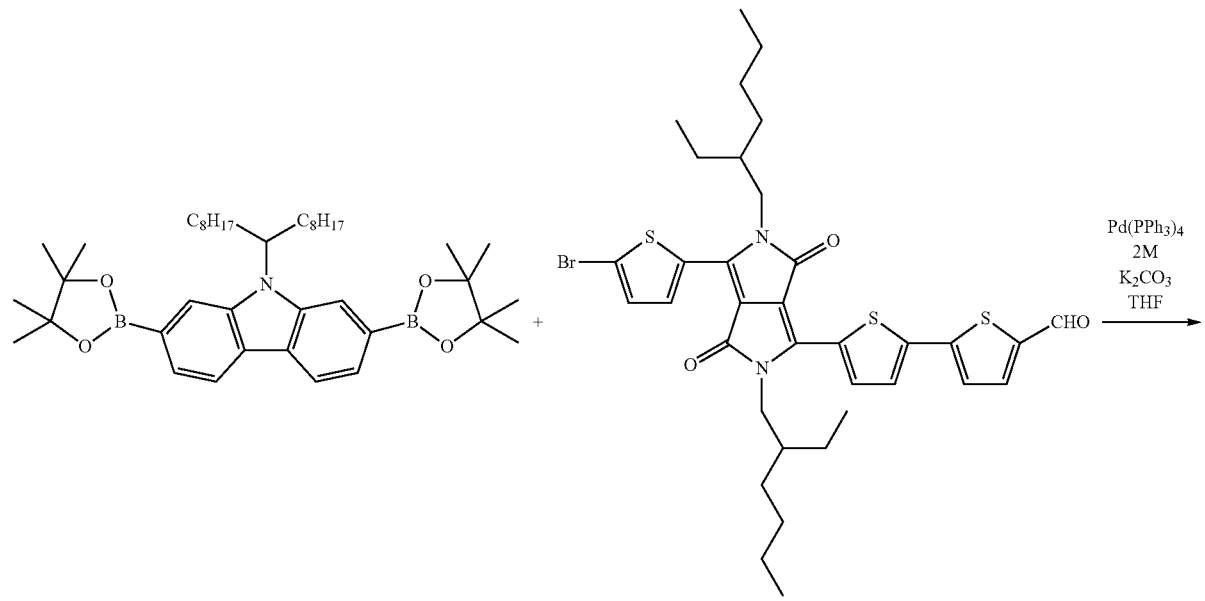

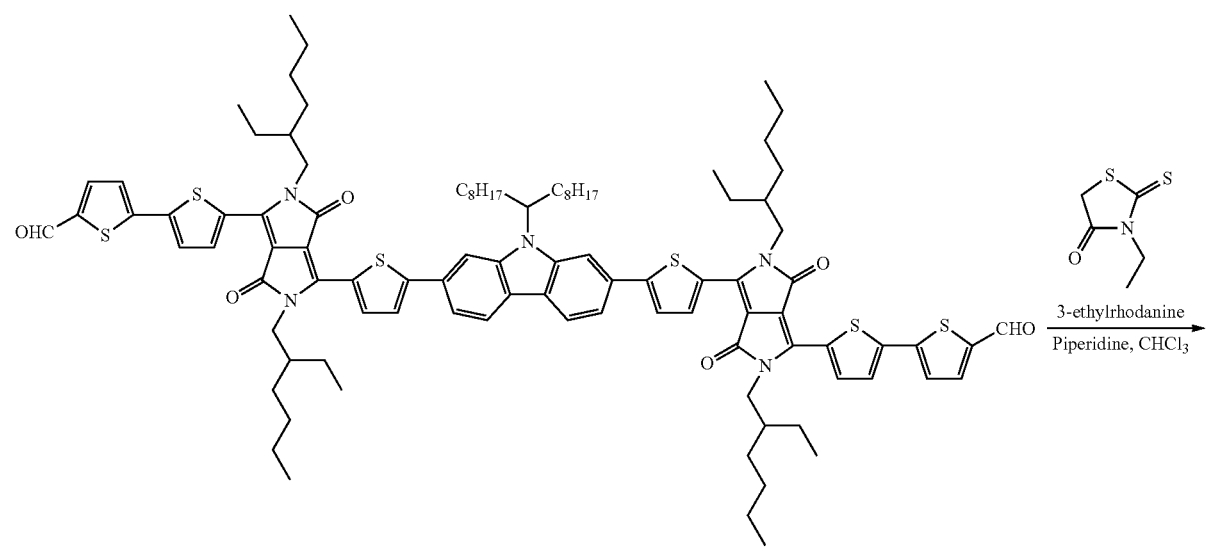

[Formula 1-A-1]

-continued

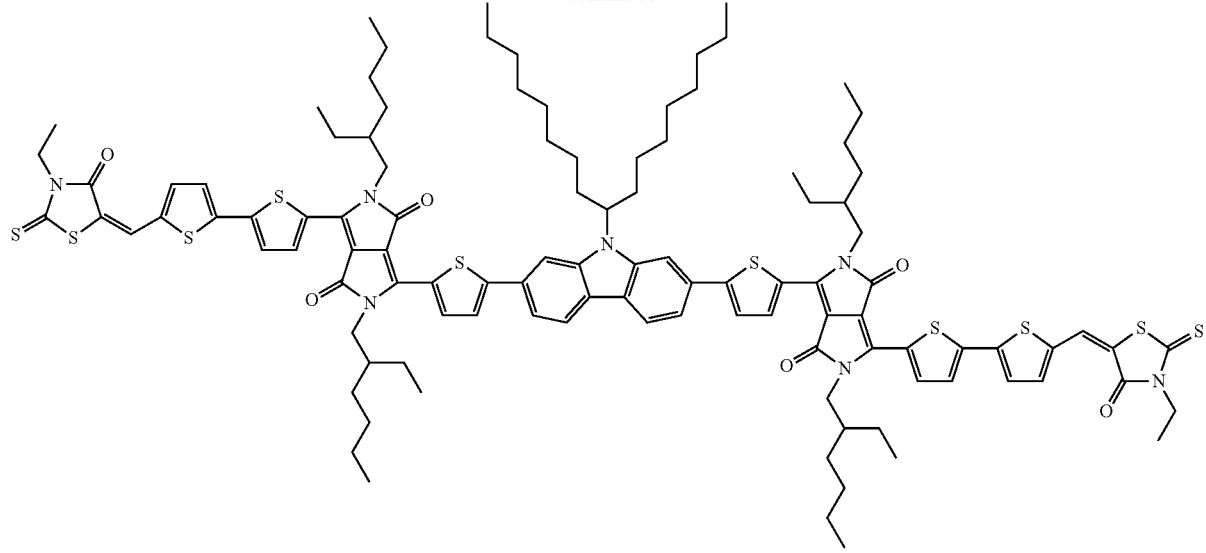

[Formula 1-1-1]

(1) 9-(heptadecan-9-yl)-2,7-bis(4,4,5,5-tetramethyl-1,3,2-dioxaborolan-2-yl)-9H-carbazole (0.46 g, 0.7 mmol) and Formula A (1.07 g, 1.5 mmol) were dissolved in 30 mL of THF, a tetrakis(triphenylphosphine)palladium (0) (Pd(PPh$_3$)$_4$) catalyst (0.0578 g, 0.05 mmol) was added thereto, 7.5 mL of 2 M K$_2$CO$_3$ was added thereto, and the resulting solution was stirred at 70° C. for 48 hours.

After the reaction was performed, an extraction was performed with dichloromethane (DCM), the remaining water was removed over magnesium sulfate (MgSO$_4$), and then the solvent was removed under reduced pressure. A brown Formula 1-A-1 was obtained by subjecting the remaining product to silica column (eluent: DCM to CHCl$_3$). (Yield: 59%)

(2) Formula 1-A-1 (0.401 g, 0.24 mmol), three drops of piperidine, and 3-ethylrhodanine (0.743 g, 4.61 mmol) were put into 25 mL of chloroform (CHCl$_3$), and the resulting solution was refluxed under nitrogen for 24 hours. After the reaction was performed, the solution was extracted with dichloromethane (DCM), the remaining water was removed over magnesium sulfate (MgSO$_4$), and then the solvent was removed under reduced pressure. A dark purplish brown solid Formula 1-1-1 was obtained by subjecting the remaining product to silica column (eluent: CHCl$_3$: EA gradient).

FIG. 2 is a view illustrating the NMR data of Formula 1-A-1.

FIG. 3 is a view illustrating the MS spectrum of Formula 1-1-1.

Preparation Example 4. Preparation of Formula 1-1-2

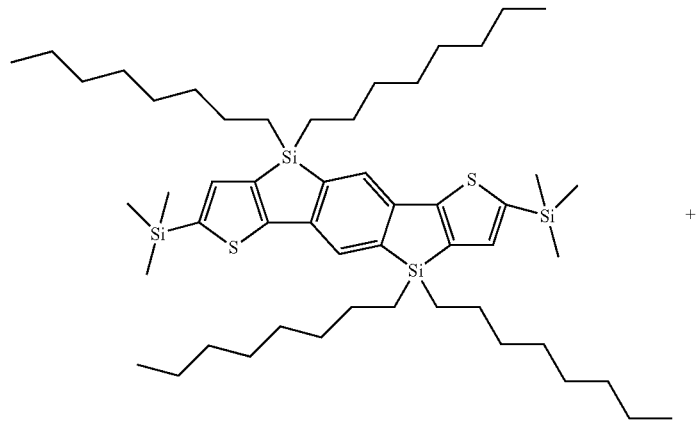

[Formula B]

+

-continued
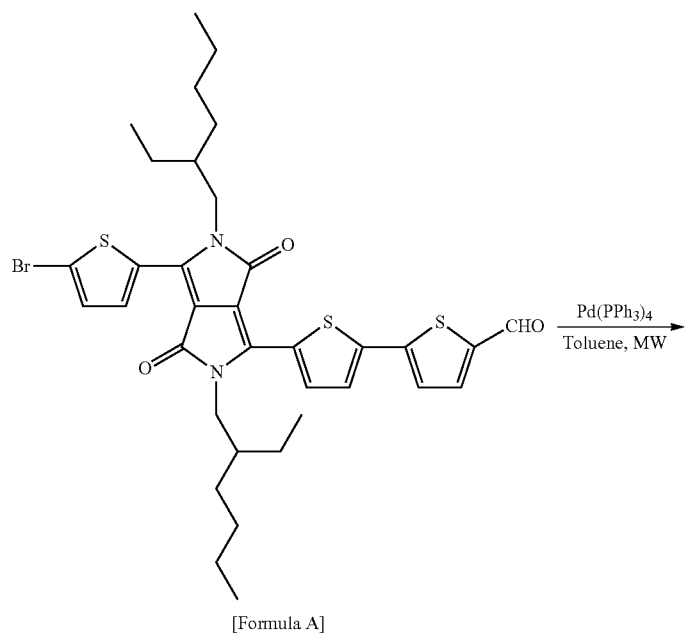
[Formula A]
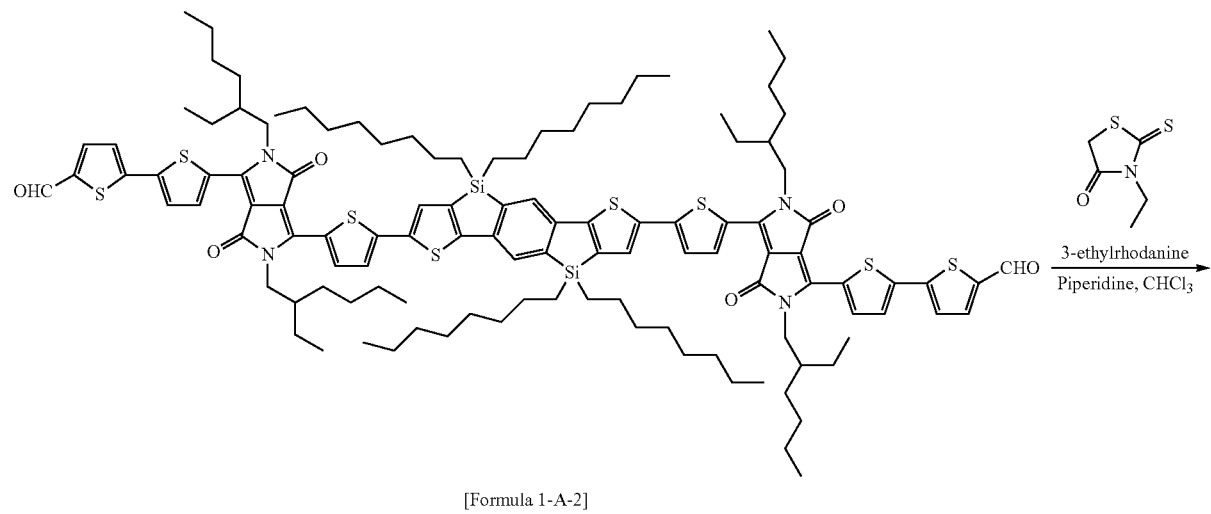
[Formula 1-A-2]
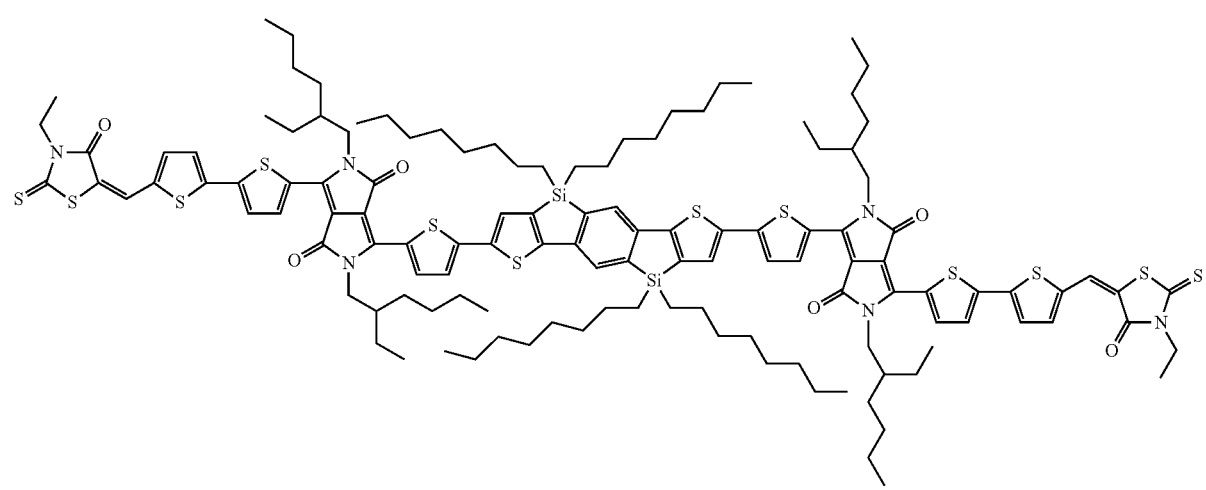
[Formula 1-1-2]

(1) Formula B (0.504 g, 0.47 mmol) and Formula A (0.79 g, 1.1 mmol) were dissolved in 15 mL of toluene, a tetrakis (triphenylphosphine) palladium (0) (Pd(PPh$_3$)$_4$) catalyst (0.023 g, 0.02 mmol) was added thereto, and the resulting solution was stirred at 80° C. for 5 minutes, at 100° C. for 5 minutes, at 120° C. for 5 minutes, at 130° C. for 5 minutes, and at 150° C. for 1 hour in a microwave reactor. After the reaction was performed, the reaction solution was poured into methanol to obtain a precipitate, and then a dark blue solid Formula 1-A-2 was obtained by filtering the precipitated solid, washing the filtered solid with methanol, and subjecting the product to silica column (eluent: DCM to CHCl$_3$).

(2) Formula 1-A-2 (0.523 g, 0.26 mmol), three drops of piperidine, and 3-ethylrhodanine (0.806 g, 5.0 mmol) were put into 80 mL of chloroform (CHCl$_3$), and the resulting solution was refluxed under nitrogen for 24 hours. After the reaction was performed, the solution was extracted with dichloromethane (DCM), the remaining water was removed over magnesium sulfate (MgSO$_4$), and then the solvent was removed under reduced pressure. A dark purple solid Formula 1-1-2 was obtained by subjecting the remaining product to silica column (eluent: CHCl$_3$: EA gradient).

FIG. 4 is a view illustrating the MS spectrum of Formula 1-1-2.

FIG. 5 is a view illustrating the differential scanning calorimetry (DSC) of Formula 1-1-2.

As can be seen in FIG. 5, the exothermic peak rising up in the vicinity of 210° C. indicates a crystallization temperature (Tc), and it can be confirmed through this that the material is crystalline. Accordingly, due to crystallinity of the heterocyclic compound according to an exemplary embodiment of the present specification, it is possible to expect that the fill factor (FF) is increased. FIG. 6 is a view illustrating the NMR graph of Formula 1-1-2.

Comparative Example 1

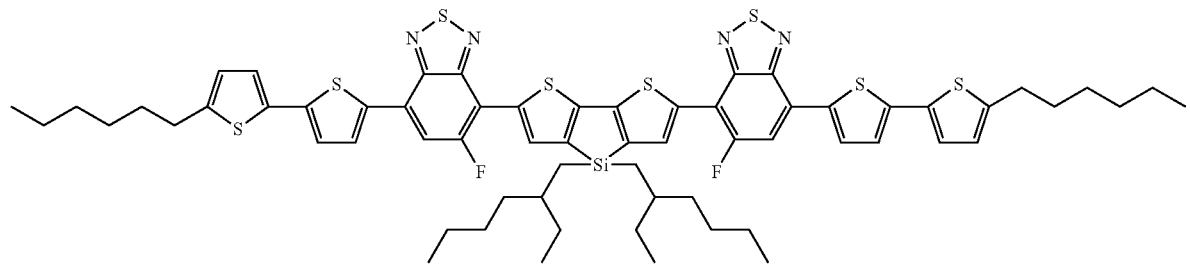 [SMILES: CCCCCCc1ccc(-c2ccc(-c3cc(F)c(-c4cc5c(s4)-c4sc(-c6c(F)cc(-c7ccc(-c8ccc(CCCCCC)s8)s7)c7nsnc67)cc4[Si]5(CC(CC)CCCC)CC(CC)CCCC)c4nsnc34)s2)s1]

FIG. 7 is a view illustrating absorption spectra of Comparative Example 1 in a solution state and Formula 1-1-2.

FIG. 8 is a view illustrating absorption spectra of Comparative Example 1 in a solid state and Formula 1-1-2.

As can be seen in FIGS. 7 and 8, it can be confirmed that in the case of the compound according to an exemplary embodiment of the present specification, long waves may be absorbed due to the occurrence of a red shift in the absorption spectrum. In this case, the molar extinction coefficient is large and the band gap is decreased, and thus, a large amount of light may be absorbed, thereby positively affecting an increase in efficiency of the device.

FIG. 9 is a view illustrating the incident photon-to-current efficiency (IPCE) of an organic solar cell using Formula 1-1-2.

Further, as can be seen in FIGS. 7 to 9, it can be confirmed that the heterocyclic compound is advantageous in implementing an organic solar cell with high efficiency because it is possible to absorb light with a broad spectrum in a range of 300 nm to 800 nm, which is not only the entire visible light region, but also in a near-infrared (NIR) range.

In addition, it can be confirmed through FIG. 8 that a red shift occurs even in the absorption spectrum because the molecular interaction is generated due to the crystallinity of the heterocyclic compound of the present specification in a solid state.

Comparative Example 2
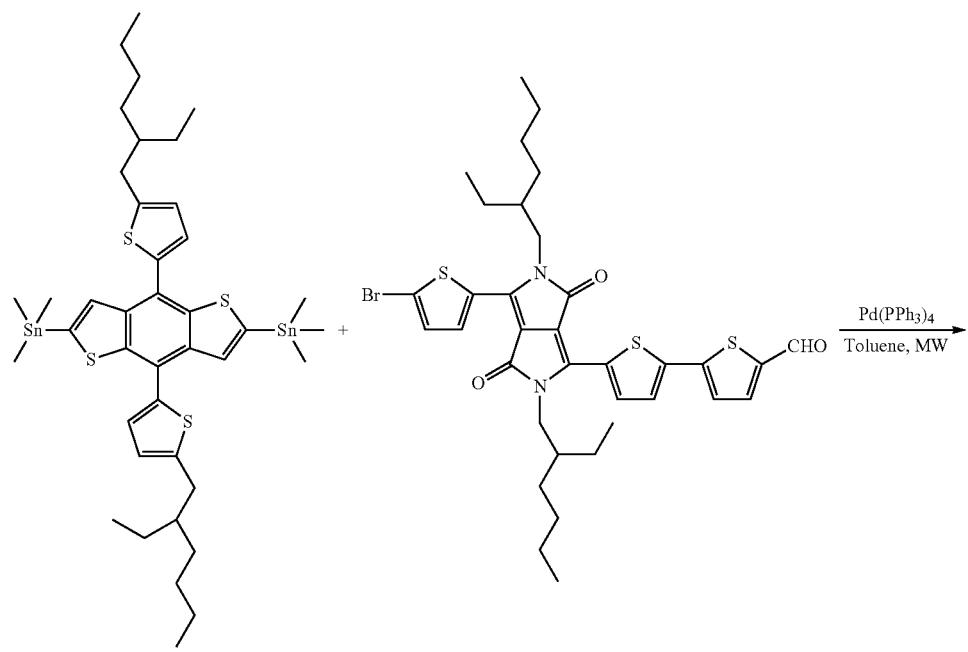
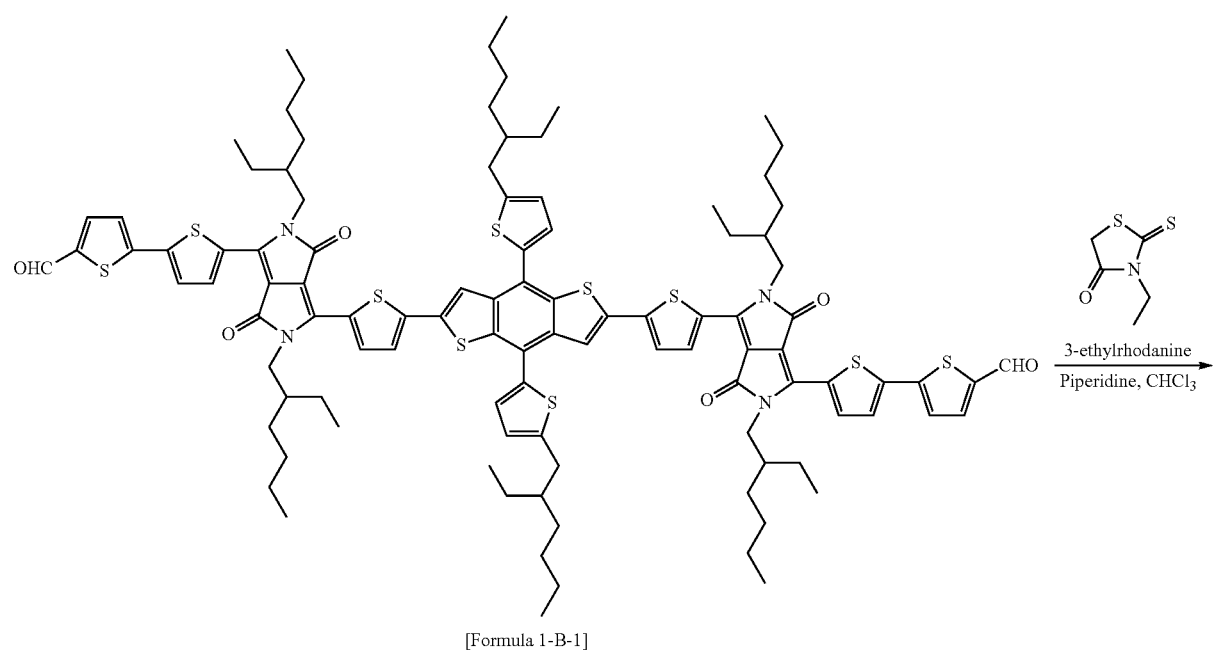
[Formula 1-B-1]

-continued

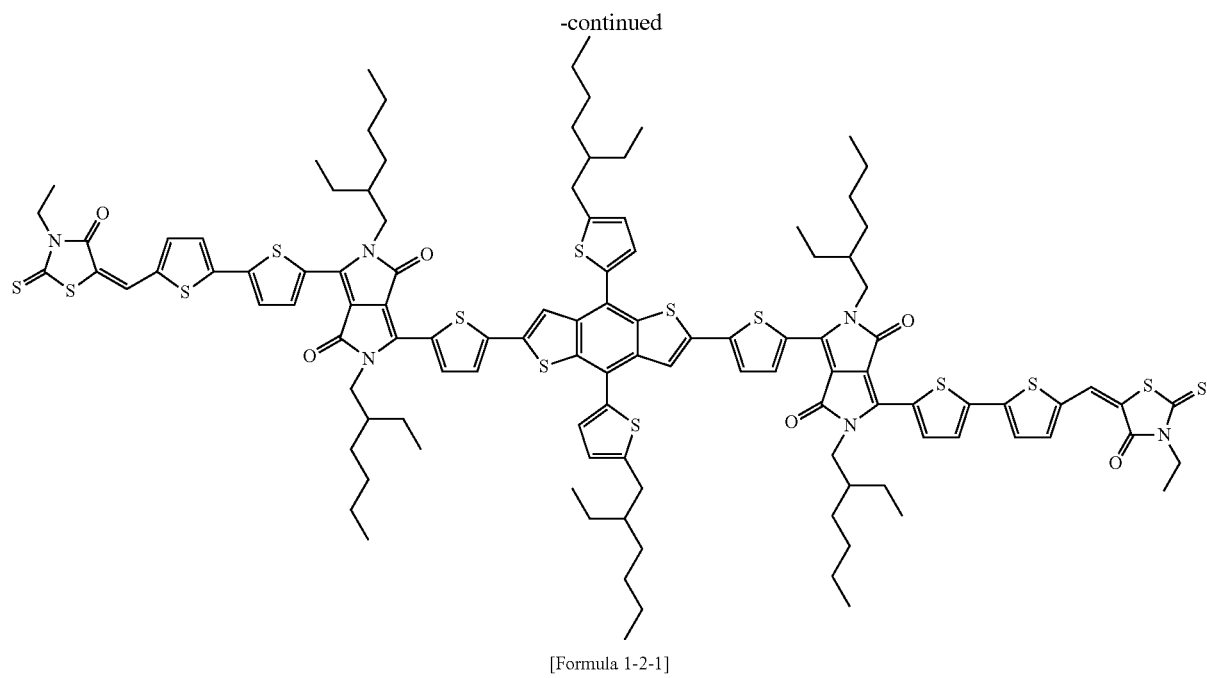

[Formula 1-2-1]

(1) Tin-benzodithiophene (Tin-BDT) (0.543 g, 0.6 mmol) and Formula A (0.93 g, 1.3 mmol) were dissolved in 15 mL of toluene, a tetrakis (triphenylphosphine) palladium (0) (Pd(PPh$_3$)$_4$) catalyst (0.023 g, 0.02 mmol) was added thereto, and the resulting solution was stirred at 80° C. for 5 minutes, at 100° C. for 5 minutes, at 120° C. for 5 minutes, at 130° C. for 5 minutes, and at 150° C. for 1 hour in a microwave reactor. After the reaction was performed, the reaction solution was poured into methanol to obtain a precipitate, and then a green solid Formula 1-B-1 was obtained by filtering the precipitated solid, washing the filtered solid with methanol, and subjecting the product to silica column (eluent: DCM to CHCl$_3$).

(2) Formula 1-B-1 (0.608 g, 0.33 mmol), three drops of piperidine, and 3-ethylrhodanine (1.064 g, 6.6 mmol) were put into 80 mL of chloroform (CHCl$_3$), and the resulting solution was refluxed under nitrogen for 24 hours. After the reaction was performed, the solution was extracted with dichloromethane (DCM), the remaining water was removed over magnesium sulfate (MgSO$_4$), and then the solvent was removed under reduced pressure. A dark purplish brown solid Formula 1-2-1 was obtained by subjecting the remaining product to silica column (eluent: CHCl$_3$: EA gradient).

FIG. 10 is a view illustrating the MS spectrum of Formula 1-2-1.

FIG. 11 is a view illustrating the differential scanning calorimetry (DSC) of Formula 1-2-1.

When FIG. 5 is compared with FIG. 11, in the case of the heterocyclic compound of Formula 1-1-2 according to an exemplary embodiment of the present specification, the crystallization temperature (Tc) may be confirmed through the exothermic peak rising up in the vicinity of 210° C. However, in the differential scanning calorimetry of the heterocyclic compound of Formula 1-2-1, a peak as in FIG. 5 was not observed.

Accordingly, it can be confirmed that the heterocyclic compound according to an exemplary embodiment of the present specification is crystalline.

Experimental Example 1. Manufacture of Organic Solar Cell and Measurement of Characteristics Thereof A composite solution was prepared by using the prepared compound as an electron donor and PC$_{60}$BM as an electron acceptor while setting the blending ratio to 1:2 (w/w ratio), and dissolving the mixture in chloroform (CF). In this case, the concentration was adjusted to 2.0 wt %, and the organic solar cell was made to have a structure of ITO/PEDOT:PSS/a photoactive layer/Al. A glass substrate coated with ITO was ultrasonically washed using distilled water, acetone, and 2-propanol, and the ITO surface was treated with ozone for 10 minutes, followed by heat treatment at 235° C. for 5 minutes by spin-coating PEDOT:PSS (AI4083) with a thickness of 45 nm at 4,000 rpm for 40 seconds. In order to coat the photoactive layer, a compound-PCBM composite solution was filtered with a 0.45 μm PP syringe filter and spin-coated, and then an organic solar cell was manufactured by depositing Al to a thickness of 100 nm using a thermal evaporator under a vacuum of 3×10$^{-8}$ torr.

TABLE 1

|  |  |  | $V_{OC}$ | $J_{SC}$ | FF | PCE |
|---|---|---|---|---|---|---|
|  | Active layer |  |  |  |  |  |
|  | Polymer:PC$_{60}$BM | rpm | (V) | (mA/cm$^2$) | (%) | (%) |
| Experimental Example 1 | Formula 1-1-1:PC$_{60}$BM = 1:2 (2 wt %) | 1000 | 0.795 | 4.392 | 0.715 | 2.5 |
|  |  |  | 0.786 | 5.15 | 0.711 | 2.88 |
|  |  |  | 0.797 | 4.703 | 0.706 | 2.65 |
|  |  |  | 0.785 | 4.938 | 0.706 | 2.74 |
|  |  | 1200 | 0.781 | 4.696 | 0.706 | 2.59 |
|  |  |  | 0.783 | 6.072 | 0.688 | 3.27 |
|  |  |  | 0.805 | 7.155 | 0.665 | 3.83 |
|  |  |  | 0.783 | 6.725 | 0.657 | 3.46 |
| Comparative Example 1 | Formula 1-2-1:PC$_{60}$BM = 1:2 (2 wt %) in CB | 1000 | 0.621 | 1.602 | 0.489 | 0.46 |
|  |  |  | 0.759 | 1.747 | 0.502 | 0.63 |
|  |  |  | 0.782 | 1.978 | 0.488 | 0.72 |
|  |  |  | 0.749 | 1.744 | 0.508 | 0.63 |
|  |  |  | 0.769 | 1.726 | 0.507 | 0.64 |
|  |  |  | 0.766 | 1.902 | 0.46 | 0.63 |
|  | Formula 1-2-1:PC$_{60}$BM = 1:2 (2 wt %) in CB SVA 1 min | 1000 | 0.683 | 1.717 | 0.461 | 0.51 |
|  |  |  | 0.656 | 1.587 | 0.394 | 0.39 |
|  |  |  | 0.734 | 1.807 | 0.456 | 0.57 |
|  | Formula 1-2-1:PC$_{70}$BM = 1:2 (2 wt %) in CB | 1000 | 0.741 | 2.672 | 0.394 | 0.74 |
|  |  |  | 0.448 | 2.476 | 0.36 | 0.38 |
|  |  |  | 0.769 | 2.858 | 0.417 | 0.87 |
|  |  |  | 0.685 | 2.429 | 0.344 | 0.54 |
|  |  |  | 0.366 | 2.267 | 0.347 | 0.27 |
|  |  |  | 0.749 | 2.746 | 0.347 | 0.68 |
|  | Formula 1-2-1:PC$_{70}$BM = 1:2 (2 wt %) in CB SVA 1 min | 1000 | 0.769 | 2.389 | 0.426 | 0.74 |
|  |  |  | 0.573 | 2.2 | 0.397 | 0.47 |
|  |  |  | 0.792 | 2.7 | 0.514 | 1.04 |
|  | Formula 1-2-1:PC$_{60}$BM = 1:2 (2 wt %) in CF | 1200 | 0.7 | 1.505 | 0.428 | 0.43 |
|  |  |  | 0.716 | 1.521 | 0.397 | 0.41 |
|  |  |  | 0.748 | 1.751 | 0.412 | 0.51 |
|  |  |  | 0.667 | 1.785 | 0.481 | 0.54 |
|  |  |  | 0.714 | 1.624 | 0.466 | 0.51 |
|  |  |  | 0.75 | 1.631 | 0.484 | 0.56 |
|  | Formula 1-2-1:PC$_{60}$BM = 1:2 (2 wt %) in CF SVA 1 min | 1200 | 0.735 | 1.413 | 0.465 | 0.46 |
|  |  |  | 0.757 | 1.463 | 0.455 | 0.48 |
|  |  |  | 0.775 | 1.538 | 0.482 | 0.56 |
|  | Formula 1-2-1:PC$_{70}$BM = 1:2 (2 wt %) in CF | 1200 | 0.753 | 0.854 | 0.516 | 0.31 |
|  |  |  | 0.749 | 0.859 | 0.479 | 0.29 |
|  |  |  | 0.765 | 0.864 | 0.506 | 0.32 |
|  |  |  | 0.756 | 0.942 | 0.459 | 0.31 |
|  |  |  | 0.7 | 0.983 | 0.363 | 0.24 |
|  |  |  | 0.761 | 0.963 | 0.461 | 0.32 |
|  | Formula 1-2-1:PC$_{70}$BM = 1:2 (2 wt %) in CF SVA 1 min | 1200 | 0.642 | 0.680 | 0.488 | 0.2 |
|  |  |  | 0.683 | 0.727 | 0.507 | 0.24 |
|  |  |  | 0.703 | 0.705 | 0.389 | 0.18 |

In Table 1, Voc, Jsc, FF, and PCE mean an open-circuit voltage, a short-circuit current, a fill factor, and energy conversion efficiency, respectively. Further, CB means a solution obtained by dissolving the compound and PCBM in chlorobenzene, CF means a solution obtained by dissolving the compound and PCBM in chloroform, and SVA means a product subjected to solvent vapor annealing.

The open-circuit voltage and the short-circuit current are an X axis intercept and an Y axis intercept, respectively, in the fourth quadrant of the voltage-current density curve, and as the two values are increased, the efficiency of the solar cell is preferably increased. In addition, the fill factor is a value obtained by dividing the area of a rectangle, which may be drawn within the curve, by the product of the short-circuit current and the open-circuit voltage. The energy conversion efficiency may be obtained when these three values are divided by the intensity of the irradiated light, and the higher value is preferred.

FIG. 12 is a view illustrating the current density according to the voltage of the organic solar cell using Formula 1-1-2.

FIG. 13 is a view illustrating the current density according to the voltage of the organic solar cell using Formula 1-2-1.

The invention claimed is:

1. An organic solar cell comprising:

a first electrode;

a second electrode provided to face the first electrode; and one or more organic material layers provided between the first electrode and the second electrode and comprising a photoactive layer, wherein the one or more organic material layers comprise a heterocyclic compound of Formula 1-1 or 1-2:

[Formula 1-1]

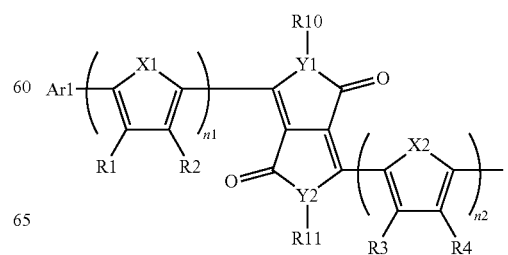

-continued

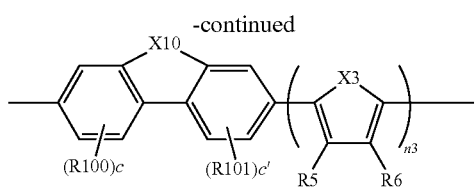

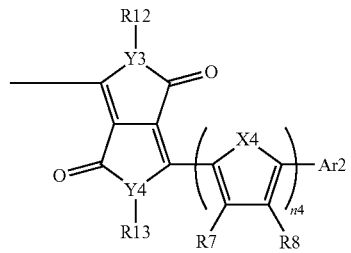

[Formula 1-2]

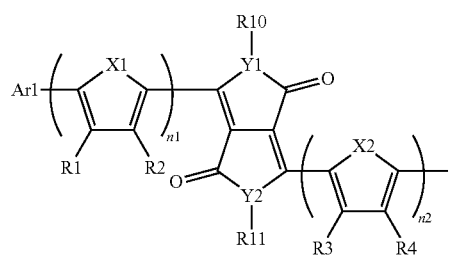

wherein:
n1 and n4 each independently is 2 or 3;
n2 and n3 each is 1;
X1 to X4 are S;
X10 and X13 of Formula 1-2 are S;

X10 of Formula 1-1 is NRa;
X11 and X12 of Formula 1-2 are SiRaRb;
Y1 to Y4 are N;
R1 to R8 are hydrogen;
Ra, Rb and R10 to R13 are the same as or different from each other, and each independently is an alkyl group;
Ar1 and Ar2 are the same as or different from each other, and each independently is:

![structure showing thiazolidine with S, N—R14, O groups]

wherein:
R14 is an alkyl group; and
R100 to R103 are the same as or different from each other, and each independently is hydrogen, deuterium, a halogen group, a nitrile group, a nitro group, an imide group, an amide group, a hydroxyl group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, or a substituted or unsubstituted heterocyclic group.

2. The organic solar cell of claim 1, wherein R10 to R13 are the same as or different from each other, and are each independently a straight-chained or branched alkyl group having 4 to 30 carbon atoms.

3. The organic solar cell of claim 1, wherein R10 to R13 are the same as or different from each other, and are each independently a straight-chained or branched alkyl group having 6 to 16 carbon atoms, and
R14 is an alkyl group having 1 to 16 carbon atoms.

4. The organic solar cell of claim 1, wherein the heterocyclic compound of Formula 1-1 or 1-2 is a compound of Formula 1-1-1 or 1-1-2, respectively:

[Formula 1-1-1]

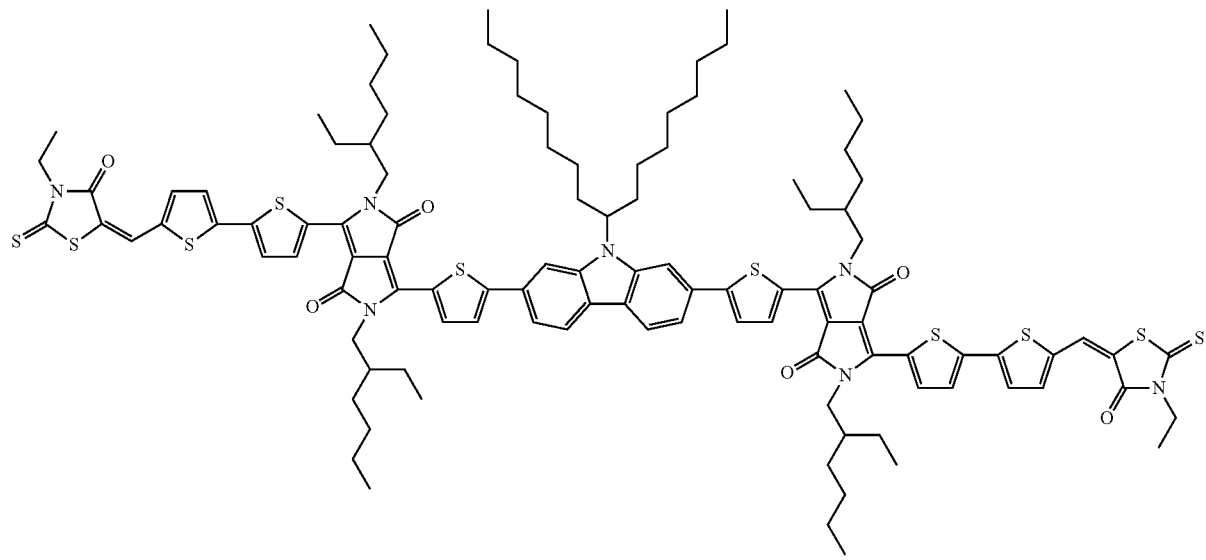

[Formula 1-1-2]

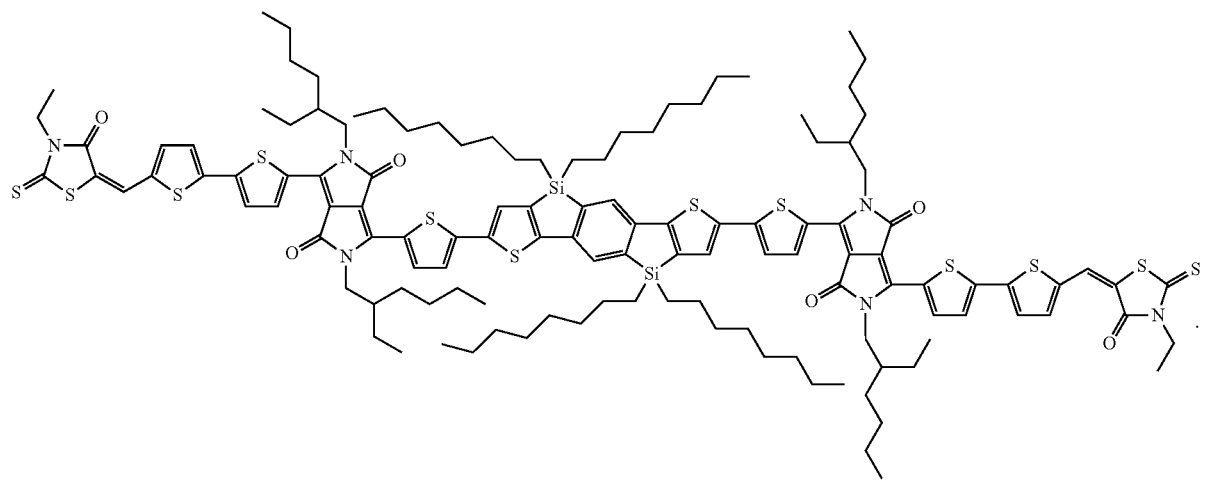

5. The organic solar cell of claim 1, wherein the one or more organic material layers comprise a hole transport layer, a hole injection layer, or a layer which simultaneously transports and injects holes, and the hole transport layer, the hole injection layer, or the layer which simultaneously transports and injects holes comprises the heterocyclic compound.

6. The organic solar cell of claim 1, wherein the one or more organic material layers comprise an electron injection layer, an electron transport layer, or a layer which simultaneously injects and transports electrons, and the electron injection layer, the electron transport layer, or the layer which simultaneously injects and transports electrons comprises the heterocyclic compound.

7. The organic solar cell of claim 1, wherein the photoactive layer comprises one or two or more selected from the group consisting of an electron donor and an electron acceptor, and the electron donor comprises the heterocyclic compound.

8. The organic solar cell of claim 7, wherein the electron donor and the electron acceptor constitute a bulk heterojunction (BHJ).

9. The organic solar cell of claim 1, wherein the photoactive layer has a bilayer thin film structure comprising an n-type organic material layer and a p-type organic material layer, and the p-type organic material layer comprises the heterocyclic compound.

10. The organic solar cell of claim 1, wherein the one or more layers of the organic material layers comprise the heterocyclic compound of Formula 1-1.

11. The organic solar cell of claim 10, wherein the heterocyclic compound of Formula 1-1 is a compound of Formula 1-1-1:

[Formula 1-1-1]
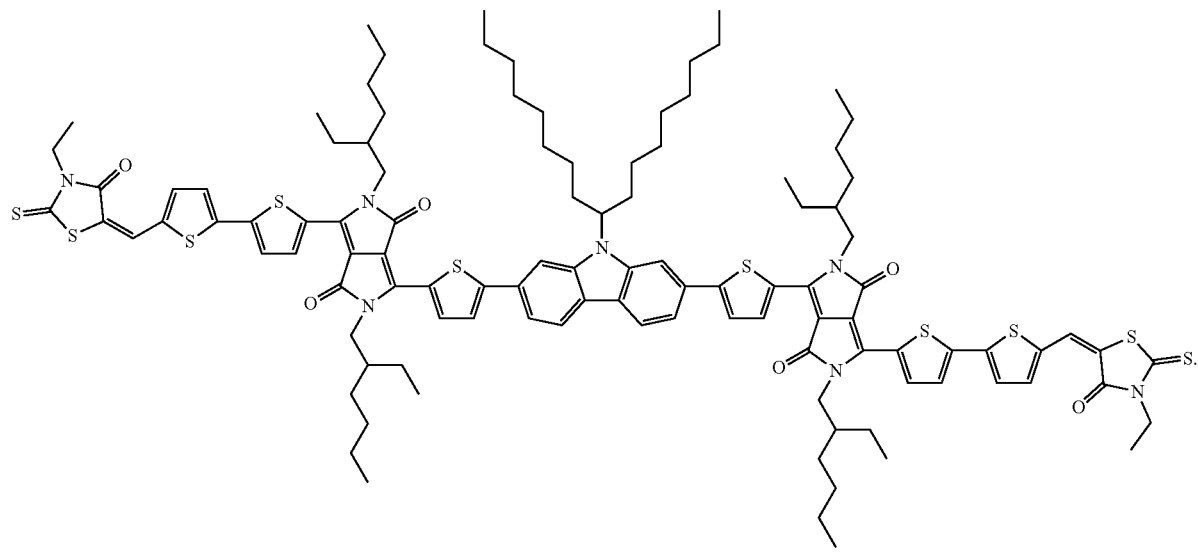
12. The organic solar cell of claim 1, wherein the one or more organic material layers comprise the heterocyclic compound of Formula 1-2.
13. The organic solar cell of claim 12, wherein the heterocyclic compound of Formula 1-2 is a compound of Formula 1-1-2:
[Formula 1-1-2]
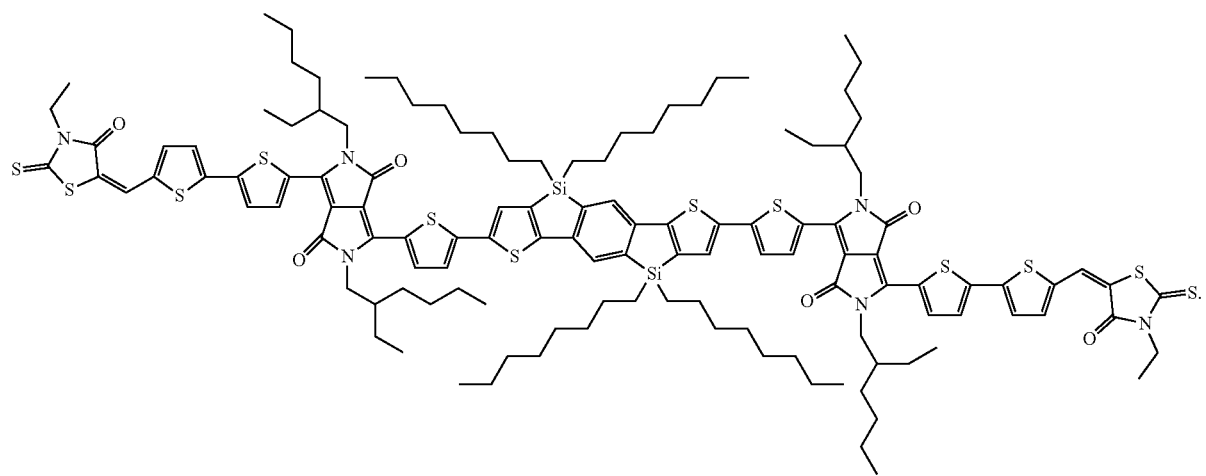
* * * * *

UNITED STATES PATENT AND TRADEMARK OFFICE
CERTIFICATE OF CORRECTION

PATENT NO. : 10,355,221 B2
APPLICATION NO. : 14/771056
DATED : July 16, 2019
INVENTOR(S) : Lim et al.

Page 1 of 1

It is certified that error appears in the above-identified patent and that said Letters Patent is hereby corrected as shown below:

In the Claims

Column 42, Line 63, Claim 10: Please correct "more layers of the organic material" to read -- more organic material --

Signed and Sealed this
Twenty-sixth Day of November, 2019

Andrei Iancu
*Director of the United States Patent and Trademark Office*